United States Patent
Agarwal et al.

(10) Patent No.: US 10,980,776 B2
(45) Date of Patent: *Apr. 20, 2021

(54) SYNERGISTIC PHARMACEUTICAL COMBINATION FOR THE TREATMENT OF SQUAMOUS CELL CARCINOMA OF HEAD AND NECK

(71) Applicant: Piramal Enterprises Limited, Mumbai (IN)

(72) Inventors: Veena Agarwal, Mumbai (IN); Arun Balakrishnan, Mumbai (IN); Giridharan Periyasamy, Mumbai (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/270,643

(22) Filed: Feb. 8, 2019

(65) Prior Publication Data
US 2019/0167639 A1 Jun. 6, 2019

Related U.S. Application Data

(63) Continuation of application No. 15/206,185, filed on Jul. 8, 2016, now Pat. No. 10,245,251, which is a continuation of application No. 14/122,922, filed as application No. PCT/IB2012/052698 on May 30, 2012, now abandoned.

(60) Provisional application No. 61/491,569, filed on May 31, 2011.

(51) Int. Cl.
| A61K 31/4025 | (2006.01) |
| A61K 31/337 | (2006.01) |
| A61K 31/513 | (2006.01) |
| A61K 31/517 | (2006.01) |
| A61K 31/282 | (2006.01) |
| A61K 31/44 | (2006.01) |
| A61K 33/24 | (2019.01) |
| A61K 39/395 | (2006.01) |

(52) U.S. Cl.
CPC ........ *A61K 31/4025* (2013.01); *A61K 31/282* (2013.01); *A61K 31/337* (2013.01); *A61K 31/44* (2013.01); *A61K 31/513* (2013.01); *A61K 31/517* (2013.01); *A61K 33/24* (2013.01); *A61K 39/39558* (2013.01)

(58) Field of Classification Search
CPC ............ A61K 2300/00; A61K 31/4025; A61K 31/44; A61K 31/517
See application file for complete search history.

(56) References Cited

U.S. PATENT DOCUMENTS

| 10,245,251 B2 * | 4/2019 | Agarwal | A61K 31/337 |
| 2007/0015802 A1 * | 1/2007 | Lal | C07D 405/04 |
| | | | 514/365 |
| 2009/0030005 A1 * | 1/2009 | Kamb | A61K 31/198 |
| | | | 514/249 |

FOREIGN PATENT DOCUMENTS

| WO | WO 2007/0148158 | * 12/2007 |
| WO | WO 2008/139271 | * 11/2008 |
| WO | WO 2010/128443 | * 11/2010 |

OTHER PUBLICATIONS

Williamson et al. (Journal of Clinical Oncology (2010) 28(20):3330-3335).*
Harrington et al. (Journal of Clinical Oncology (2009) 27(7):1100-1107).*
Gold et al. (Cancer 2009; 115: 922-935).*
Stomach cancer—Mayoclinic.com—Apr. 9, 2011.*
GastricMALTLymphoma—LymphomaAssociation—2011.*
"Adult Brain Tumors Treatment", National Cancer Institute, pp. 1-21 (Jan. 24, 2013).*

(Continued)

*Primary Examiner* — Valerie Rodriguez-Garcia
(74) *Attorney, Agent, or Firm* — Morgan, Lewis & Bockius LLP

(57) ABSTRACT

The present invention relates to a pharmaceutical combination for use in the treatment of squamous cell carcinoma, comprising a CDK inhibitor selected from the compounds of formula (I);

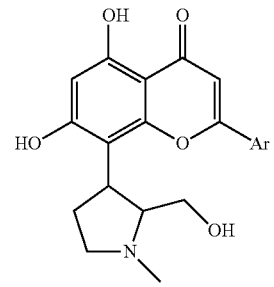

Formula I or a pharmaceutically acceptable salt thereof and one or more antineoplastic agents selected from sorafenib, lapatinib, erlotinib, cisplatin, 5-fluorouracil, docetaxel or cetuximab or a pharmaceutically acceptable salt thereof. The said pharmaceutical combination exhibits synergy when used in the treatment of squamous cell carcinoma of head and neck (SCCHN). The invention also relates to a pharmaceutical composition comprising the said combination and a method for the treatment of squamous cell carcinoma of head and neck (SCCHN), using a therapeutically effective amount of said combination.

8 Claims, 17 Drawing Sheets

(56) References Cited

OTHER PUBLICATIONS

Types of Brain Cancer at http://www.cancercenter.com/brain-cancer/types-of-brain-cancer.cfm (Mar. 12, 2013).*
Colorectal Cancer at cancer.net (published Sep. 2012), pp. 1-2.*
Types of Breast Cancer, published in breastcancer.org (Sep. 30, 2012); p. 1.*

* cited by examiner

SYNERGISTIC PHARMACEUTICAL COMBINATION FOR THE TREATMENT OF SQUAMOUS CELL CARCINOMA OF HEAD AND NECK

CROSS REFERENCE

This application is a continuation application of U.S. application Ser. No. 15/206,185, filed Jul. 8, 2016, which is a continuation application of U.S. application Ser. No. 14/122,922, filed Nov. 27, 2013, which is the U.S. National Stage of International Application No. PCT/IB2012/052698, filed May 30, 2012, published in English, which application claims the benefit of U.S. Provisional Application No. 61/491,569, filed May 31, 2011, all of which are incorporated herein by reference.

FIELD OF INVENTION

The present invention relates to a pharmaceutical combination comprising a cyclin dependent kinase (CDK) inhibitor selected from the compounds of formula I (as described herein) or a pharmaceutically acceptable salt thereof and one or more antineoplastic agents for use in the treatment of squamous cell carcinoma of head and neck (SCCHN). The pharmaceutical combination of the present invention exhibits synergy when used in the treatment of squamous cell carcinoma of head and neck (SCCHN). Thus, the present invention relates to a synergistic pharmaceutical combination. The present invention further relates to a pharmaceutical composition comprising said combination and a method of treating squamous cell carcinoma of head and neck (SCCHN) in a subject by administrating said pharmaceutical combination to said subject.

BACKGROUND OF INVENTION

Cancer is a group of diseases characterized by the unusual control of cell growth. There are over 100 different types of cancers, which are classified by the type of cells initially affected such as bladder cancer, breast cancer, colon cancer, rectal cancer, endometrial cancer, kidney (renal cell) cancer, leukemia, small cell lung cancer, non-small cell lung cancer, pancreatic cancer, prostate cancer, thyroid cancer, skin cancer, non-hodgkin's lymphoma and melanoma and head and neck cancer. Squamous cell carcinoma represents more than 90% of all head and neck cancers. Head and neck squamous cell carcinomas make up the vast majority of head and neck cancers, and arise from mucosal surfaces throughout the anatomical region. These include tumors of the nasal cavities, paranasal sinuses, oral cavity, nasopharynx, oropharynx, hypopharynx, and larynx.

In fact, head and neck cancer (HNC) is the sixth most common cancer worldwide, with an annual incidence of >640,000 cases worldwide. More than 90% of head and neck cancers are of squamous histology (HNSCC). Thirty-five percent to 45% of head and neck cancer patients ultimately die from their disease. In the United States alone, squamous cell carcinoma of the head and neck comprises about 4% of all malignancies. This corresponds to an estimated 17 per 100,000 persons with newly diagnosed squamous cell carcinoma of the head and neck per year (Jemal A, Siegel R, Ward E, et al. Cancer statistics, 2008, *CA Cancer J. Clin.* 2008 March-April; 58(2):71-96). Squamous cell carcinoma of head and neck (SCCHN) remains a challenging clinical problem, due to persisting high rate of local and distant failure, as well as the occurrence of second primaries. Some molecular targeted therapy used in squamous cell cancers of the head and neck include cetuximab, bevacizumab, erlotinib and reovirus. The best quality data are available for cetuximab, a recombinant monoclonal antibody, since the 2006 publication of a randomized clinical trial comparing radiation treatment plus cetuximab versus radiation treatment alone ("Radiotherapy plus cetuximab for squamous-cell carcinoma of the head and neck". *N Engl J Med* 2006; 354 (6): 567-78). Another study evaluated the impact of adding cetuximab to conventional chemotherapy involving use of cisplatin versus cisplatin alone. This study found no improvement in survival or disease-free survival with the addition of cetuximab to the conventional chemotherapy (*J Clin Oncol.* 2005; 23 (34): 8646-54). However, another study completed in March 2007 found that there was an improvement in survival. This study is referred to as EXTREME (Erbitux in First-Line Treatment of Recurrent or Metastatic Head and Neck Cancer) study which is a European multicenter phase III trial.

Further, it is well established in the art that CDK (Cyclin-dependent kinase) inhibitors are useful in anti-proliferative therapies for diseases characterized by excessive cell growth such as cancers and immunological disorders involving unwanted proliferation of leukocytes. Flavone derivatives useful as CDK inhibitors are described in PCT Patent Publication No. WO2004-004632 (U.S. Pat. No. 7,271,193) which patent application specifically relates to the compounds for inhibition of cyclin-dependent kinases, process for their preparation, methods of inhibiting cyclin-dependent kinases and of inhibiting cell proliferation, use of such compounds in the treatment of proliferative disorders including cancers. PCT Published application No. WO2005-053699 (U.S. Pat. No. 7,772,207) relates to a pharmaceutical product comprising a CDK inhibitor and 1-(2-C-cyano-2-dioxy-p-D-arabino-pentofuranosyl)-N4-palmitoyl cytosine or a metabolite thereof, as a combined preparation for simultaneous, sequential or separate administration. PCT Published application No. WO2008-122779 (U.S. Patent Appl. Pub. 2010-0143350) describes combination of CDK inhibitor with a tyrosine kinase inhibitor and use thereof in the treatment of proliferative disorders. PCT Published application No. WO2008-139271 (U.S. Patent Appl. Pub. 2010-0305057) relates to pharmaceutical combination comprising a cytotoxic antineoplastic agent selected from paclitaxel, docetaxel, doxorubicin or gemcitabine and at least one cyclin dependent kinase (CDK) inhibitor for use in the treatment of cancer. PCT Published application No. WO2010-128443 describes a combination for the treatment of cancer wherein the combination comprises radiation and at least one cyclin dependent kinase (CDK) inhibitor or a pharmaceutically acceptable salt or a solvate thereof.

Although combinations of anticancer agents have been proven to have a significant advance in various cancer treatment protocols including squamous-cell carcinoma of the head and neck (SCCHN), there are still several unmet needs and room for improvements in medications for the treatment of SCCHN, which are difficult to treat, or which have shown resistance to treatment with the conventional antineoplastic agents. More particularly, the development of novel combination approach for delivering known anticancer agents having different mechanism of action would represent an important advance in the art. Although the protocol involving combination of anticancer agents having different mechanism of action may work in case of some combinations, it may not work in the same manner for other combination of anticancer agents and such combination may not always result in a combination having advantageous therapeutic effects. However, the inventors of the present invention have found that a pharmaceutical combination of anticancer agents comprising a cyclin dependant kinase (CDK) inhibitor and one or more antineoplastic agent provides greater efficacy than when the CDK inhibitors or the antineoplastic agents are used alone for the treatment of squamous-cell carcinoma of the head and neck (SCCHN).

SUMMARY OF THE INVENTION

According to one aspect of the present invention, there is provided a pharmaceutical combination for use in the treatment of squamous cell carcinoma of the head and neck (SCCHN), comprising a cyclin dependent kinase (CDK) inhibitor selected from the compounds of formula (I) or a pharmaceutically acceptable salt thereof and one or more antineoplastic agents.

In another aspect, the present invention provides pharmaceutical compositions for use the treatment of squamous cell carcinoma of the head and neck (SCCHN), comprising a combination of a cyclin dependent kinase (CDK) inhibitor selected from the compounds of formula (I) or a pharmaceutically acceptable salt or solvates thereof and one or more antineoplastic agents along with at least one pharmaceutically acceptable carrier.

In another aspect, the present invention relates to a method for the treatment of squamous cell carcinoma of the head and neck (SCCHN) in a subject, comprising administering to the subject a therapeutically effective amount of a cyclin dependent kinase (CDK) inhibitor selected from the compounds of formula (I) or pharmaceutically acceptable salts thereof in combination with a therapeutically effective amount of one or more antineoplastic agents.

According to another aspect, the present invention provides pharmaceutical combination for use in the treatment of squamous cell carcinoma of the head and neck (SCCHN); comprising a therapeutically effective amount of a cyclin dependent kinase (CDK) inhibitor selected from the compounds of formula (I) or a pharmaceutically acceptable salt thereof and a therapeutically effective amount of one or more antineoplastic agents wherein said combination exhibits synergistic effect.

In yet another aspect, the present invention relates to a kit comprising a cyclin dependent kinase (CDK) inhibitor selected from the compounds of formula (I) and one or more antineoplastic agents; wherein said kit may further include a package insert comprising printed instructions directing the use of the combined treatment as a method for treating squamous cell carcinoma of the head and neck.

Other aspects and further scope of applicability of the present invention will become apparent from the detailed description to follow.

DETAILED DESCRIPTION OF THE INVENTION

Figure 1A:
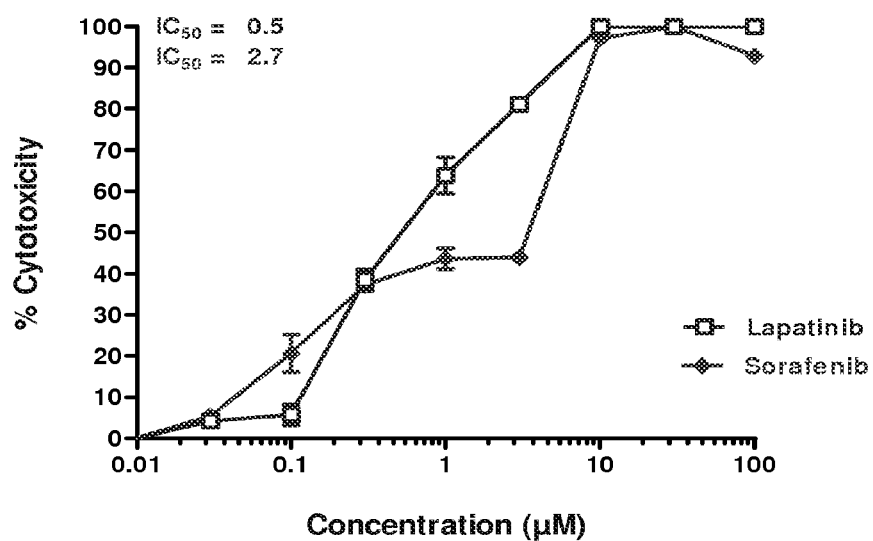
FIG. 1a is a graphical representation of the percentage inhibition results of dosing of sorafenib and lapatinib in SCC25 cells.

The present invention encompasses pharmaceutical combinations for use in the treatment of squamous cell carcinoma of the head and neck (SCCHN), comprising a cyclin dependent kinase (CDK) inhibitor selected from the compounds of formula (I) (as described herein) or a pharmaceutically acceptable salt thereof and one or more antineoplastic agents, wherein said combination exhibits synergistic effect.

According to the present invention there is provided a pharmaceutical composition for use in the treatment of squamous cell carcinoma of the head and neck (SCCHN) comprising a therapeutically effective amount of a cyclin dependent kinase (CDK) inhibitor selected from the compounds of formula (I) or a pharmaceutically acceptable salt thereof and one or more antineoplastic agents and optionally a pharmaceutically acceptable carrier.

The present invention further provides a method for the treatment of squamous cell carcinoma of head and neck in a subject, which comprises administering to the said subject a therapeutically effective amount of a CDK inhibitor selected from the compounds of formula (I) (as described herein) or a pharmaceutically acceptable salt or solvate thereof; and a therapeutically effective amount of one or more antineoplastic agents selected from the group consisting of sorafenib, lapatinib, erlotinib, cisplatin, 5-fluorouracil and docetaxel or a pharmaceutically acceptable salt thereof; wherein the said CDK inhibitor and the said antineoplastic agents contained in the combination are administered either simultaneously or sequentially.

The general terms used hereinbefore and hereinafter preferably have within the context of this disclosure the following meanings, unless otherwise indicated. Thus, the definitions of the general terms as used in the context of the present invention are provided herein below:

The singular forms "a," "an," and "the" include plural reference unless the context clearly dictates otherwise.

The phrase "a cyclin dependent kinase (CDK) inhibitor" or "CDK inhibitor" as used herein means a compound that exhibits activity against one or more known cyclin dependent kinases. In the context of the present invention the CDK inhibitor is a pyrrolidine substituted flavone compound disclosed in PCT Published Application No. WO2004004632, which application is incorporated herein by reference in its entirety. The CDK inhibitor according to the present invention is specifically selected from a compound of Formula I as described herein below or a pharmaceutically acceptable salt or solvate thereof. Further, the term "CDK inhibitor" as used herein may either refer to the compound of formula I and/or a pharmaceutically acceptable salt or solvate of the compound of formula I.

The term "antineoplastic agent" is synonymous to "a chemotherapeutic agent" or "an anticancer agent" and refers to a therapeutic agent, which acts by inhibiting or preventing the growth of neoplasms. The term "antineoplastic agent" or "anti-cancer agent" in general refers to the compounds which prevent the cancer cells from multiplying (i.e. antiproliferative agents). In general, the antineoplastic agent(s) fall into two classes, anti-proliferative cytotoxic agents and anti-proliferative cytostatic agents. Cytotoxic agents prevent cancer cells from multiplying by: (1) interfering with the cell's ability to replicate DNA; and (2) inducing cell death and/or apoptosis in the cancer cells. The cytostatic agents act via modulating, interfering or inhibiting the processes of cellular signal transduction which regulate cell proliferation.

The phrase "pharmaceutically acceptable salts" refers to the acid addition salt of compound of formula I (as described herein) and of an antineoplastic agent, wherein the acid is selected from an inorganic acid such as hydrochloric acid, hydrobromic acid; or an organic acid such as benzene sulfonic acid, maleic acid, oxalic acid, fumaric acid, succinic acid, p-toluenesulfonic acid and maleic acid.

As used herein, the term "combination" or "pharmaceutical combination", means the combined administration of the anti-cancer agents namely the CDK inhibitor selected from the compounds represented by formula I and one or more antineoplastic agents which acts by inhibiting or preventing the growth of neoplasms or the administration of the anti-cancer agents namely the CDK inhibitor selected from the compounds represented by formula I and the antineoplastic agents selected from cytostatic or cytotoxic agents; which may be administered independently at the same time or separately within time intervals that especially allow that the combination partners to show a synergistic effect.

As used herein, the term "synergistic" or "synergy" means that the effect achieved with the combinations of anticancer agents encompassed in this invention is greater than the sum of the effects that result from using anti-cancer agents namely the CDK inhibitor of formula (I) or a pharmaceutically acceptable salt thereof, antineoplastic agent(s) or a pharmaceutically acceptable salt thereof, as a monotherapy. Advantageously, such synergy provides greater efficacy at the same doses, and/or prevents or delays the build-up of multi-drug resistance.

As used herein the term "therapeutically effective amount" in reference to the treatment of squamous cell carcinoma of head and neck refers to an amount capable of invoking one or more of the following effects in a subject receiving the combination of the present invention: (i) inhibition, to some extent, of tumor growth, including, slowing down and complete growth arrest; (ii) reduction in the number of tumor cells; (iii) reduction in tumor size; (iv) inhibition (i.e., reduction, slowing down or complete stopping) of tumor cell infiltration into peripheral organs; (v) inhibition (i.e., reduction, slowing down or complete stopping) of metastasis; (vi) enhancement of anti-tumor immune response, which may, but does not have to, result in the regression of the tumor; and/or (vii) relief, to some extent, of one or more symptoms associated with squamous cell carcinoma of head and neck (SCCHN).

The term "subject" as used herein, refers to an animal, preferably a mammal, most preferably a human, who has been the object of treatment, observation or experiment. The term subject may be interchangeably used with the term "patient" in the context of the present invention.

As used herein, the term "simultaneously" means that two or more therapeutic agents (anticancer agents) are administered concurrently, "sequentially" means that two or more therapeutic agents are available to act therapeutically within the same time-frame and "separately" means that the gap between administering one agent and the other is significant i.e. the first administered agent may no longer be present in the bloodstream in a therapeutically effective amount when the second agent is administered.

The term "caspase3 activity" as used herein refers to increase in apoptosis in cancer cells.

The term "apoptosis" refers to a type of cell death in which a series of molecular steps in a cell leads to its death. This is the body's normal way of getting rid of unneeded or abnormal cells. The process of apoptosis may be blocked in cancer cells. Also called programmed cell death. (Dictionary of cancer terms, National Cancer Institute). The term "increasing apoptosis" is defined as an increase in the rate of programmed cell death, i.e. more cells are induced into the death process as compared to exposure (contact) with either the antineoplastic agent alone or the CDK inhibitor alone.

The phrase "pharmaceutically acceptable carrier" refers to one or more disintegrating agents, binders, excipients, lubricants and the like which are well known to those skilled in the art.

In the present invention there is provided a pharmaceutical combination of anti-cancer agents for use in the treatment of squamous cell carcinoma of head and neck (SCCHN). The present inventors have conducted an extensive research for the development of the pharmaceutical combination of anti-cancer agents and arrived at the present synergistic pharmaceutical combination. It has been found that pharmaceutical combination comprising a cyclin dependent kinase (CDK) inhibitor selected from the compounds of formula I or a pharmaceutically acceptable salt thereof and one or more antineoplastic agent exhibits synergistic effect when used in the treatment of squamous cell carcinoma of the head and neck (SCCHN).

The CDK inhibitor is a pyrrolidine substituted flavone compound that inhibits cyclin dependent kinases. The CDK inhibitor used in the pharmaceutical combination of the present invention is selected from the compounds of formula I or pharmaceutically acceptable salts or solvates thereof as described herein below. The compounds of formula I are promising CDK inhibitors, which can inhibit proliferation of many cancer cells. As indicated herein above the CDK inhibitors of formula (I) may be used in the form of their pharmaceutically acceptable salts. The salts encompassed within the term "pharmaceutically acceptable salts" refer to non-toxic salts of the compounds of this invention. Representative salts include, but are not limited to acetate, benzoate, benzenesulfonate, bicarbonate, chloride, citrate, hydrochloride, mesylate, methylsulfonate, tartrate, tosylate and trifluoroacetate. Preferred salts of formula (I) include hydrochloride salt, methanesulfonic acid and trifluoroacetic acid salt.

In one embodiment, the CDK inhibitor used in the pharmaceutical combination of the present invention is selected from the compounds represented by the following formula I,

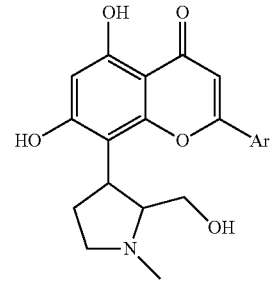

Formula I wherein, Ar is a phenyl group, which is unsubstituted or substituted by 1, 2, or 3 identical or different substituents selected from: halogen, nitro, cyano, $C_1$-$C_4$-alkyl, trifluoromethyl, hydroxyl or $C_1$-$C_4$-alkoxy; or a pharmaceutically acceptable salt or solvate thereof.

As indicated herein above the salts of CDK inhibitor refers to non-toxic salts of the compounds of formula (I) of this invention. Representative salts include, but are not limited to acetate, benzoate, benzenesulfonate, bicarbonate, chloride, citrate, hydrochloride, mesylate, methylsulfonate, tartrate, tosylate and trifluoroacetate. Preferred salts of compounds of formula (I) include hydrochloride salt, methanesulfonic acid and trifluoroacetic acid salt.

In an embodiment of the invention, the CDK inhibitor is the (+)-trans isomer of the compound of formula I, as indicated in Formula IA below,

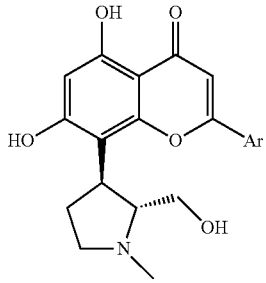

Formula IA wherein Ar is a phenyl group, which is unsubstituted or substituted by 1, 2, or 3 identical or different substituents selected from: halogen, nitro, cyano, $C_1$-$C_4$-alkyl, trifluoromethyl, hydroxyl or $C_1$-$C_4$-alkoxy; or a pharmaceutically acceptable salt or solvate thereof.

In another embodiment of the present invention, the CDK inhibitor used in the pharmaceutical combination of the present invention is a compound of formula I wherein the phenyl group is substituted by 1, 2 or 3 identical or different substituents selected from: chlorine, bromine, fluorine or iodine, $C_1$-$C_4$-alkyl or trifluoromethyl; or a pharmaceutically acceptable salt or solvate thereof.

In another embodiment of the present invention, the CDK inhibitor used in the pharmaceutical combination of the present invention is a compound of formula I wherein the phenyl group is substituted by chlorine; or a pharmaceutically acceptable salt or solvate thereof.

In another embodiment of the present invention, the CDK inhibitor used in the pharmaceutical combination of present invention is a compound of formula I wherein the phenyl group is substituted by two different substituents selected from chlorine and trifluoromethyl; or a pharmaceutically acceptable salt or solvate thereof.

It will be appreciated by those skilled in the art that the CDK inhibitors represented by the compounds of formula (I) contain at least two chiral centers and hence, exist in the form of two different optical isomers (i.e. (+) or (−) enantiomers). All such enantiomers and mixtures thereof including racemic mixtures are included within the scope of the invention. The enantiomers of the compound of formula I can be obtained by methods disclosed in PCT Application Publication No. WO2004004632 incorporated herein by reference or the enantiomers of the compound of formula I can also be obtained by methods well known in the art, such as chiral HPLC and enzymatic resolution.

Alternatively, the enantiomers of the compounds of formula I can be synthesized by using optically active starting materials. The manufacture of the compounds of formula I, which may be in the form of pharmaceutically acceptable salts and solvates, and the manufacture of oral and/or parenteral pharmaceutical composition containing the above compounds are generally disclosed in PCT Application Publication No. WO2004004632. This patent application, which is incorporated herein by reference, discloses that the CDK inhibitors represented by formula I exhibit significant anticancer efficacy. As indicated herein above the CDK inhibitors of formula I may be used in the form of their salts. Preferred salts of compounds of formula I include hydrochloride, methanesulfonic acid and trifluoroacetic acid salt.

According to another embodiment of the present invention, the CDK inhibitor used in the pharmaceutical combination of the present invention is selected from (+)-trans-2-(2-Chloro-phenyl)-5,7-dihydroxy-8-(2-hydroxy-methyl-1-methyl-pyrrolidin-3-yl)-chromen-4-one hydrochloride (referred to herein as compound A) or (+)-trans-3-[2[(2-Chloro-4-trifluoromethyl-phenyl)-5,7-dihydroxy-8-(2-hydroxymethyl-1-methyl-pyrrolidin-3-yl)-chromen-4-one hydrochloride (referred to herein as compound B).

In an embodiment of the present invention, the CDK inhibitor used in the pharmaceutical combination is (+)-trans-2-(2-Chloro-phenyl)-5,7-dihydroxy-8-(2-hydroxymethyl-1-methyl-pyrrolidin-3-yl)-chromen-4-one hydrochloride (compound A).

In further embodiment of the present invention, the CDK inhibitor used in the pharmaceutical combination is (+)-trans-3-[2[(2-Chloro-4-trifluoromethyl-phenyl)-5,7-dihydroxy-8-(2-hydroxymethyl-1-methyl-pyrrolidin-3-yl)-chromen-4-one hydrochloride (compound B).

The antineoplastic agents are the compounds that prevent cancer cells from multiplying (i.e. anti-proliferative agents). In the present invention anti-neoplastic agent included in the pharmaceutical combination may be selected from either cytostatic or cytotoxic agents.

According to an embodiment of the invention, an antineoplastic agent used in the pharmaceutical combination of the present invention is a cytostatic agent.

According to another embodiment of the invention, an anti-neoplastic agent used in the pharmaceutical combination of the present invention is a cytotoxic agent.

According to an embodiment of the invention, when the anti-neoplastic agent used in the pharmaceutical combination of the present invention is a cytostatic agent, it is selected from small molecules such as sorafenib, lapatinib or erlotinib or a chimeric monoclonal antibody such as cetuximab.

According to another embodiment of the invention, when the anti-neoplastic agent used in the pharmaceutical combination of the present invention is a cytotoxic agent, it is selected from cisplatin, 5-fluorouracil and/or docetaxel or pharmaceutically acceptable salts thereof.

According to another embodiment of the invention, the pharmaceutical combination comprising a CDK inhibitor selected from the compounds of formula (I) or a pharmaceutically acceptable salt thereof, and one or more antineoplastic agents, may further include use of radiation therapy for the treatment of squamous cell carcinoma of the head and neck (SCCHN).

The specified anti-neoplastic agents used in the present invention are commercially readily available.

Sorafenib is a kinase inhibitor that decreases tumor cells proliferation in vitro. Sorafenib was shown to inhibit multiple intracellular (CRAF, BRAF and mutant BRAF) and cell surface kinases (KIT, FLT-3, RET, VEGFR-1 to 3 and PDGFR-β. Several of these kinases are thought to be involved in tumor cell signaling, angiogenesis and apoptosis. Sorafenib inhibited tumor growth and angiogenesis of human hepatocellular carcinoma and renal cell carcinoma and several other human tumor xenografts in immunocompromised mice. It is chemically named as 4-(4-{3-[4-chloro-3-(trifluoromethyl)phenyl]ureido}phenoxy)$N^2$-methylpyridine-2-carboxamide-4-methylbenzenesulfonate. Sorafenib is commercially available and is marketed as Nexavar® by Bayer in the United States for the treatment of patients with advanced renal cell carcinoma (RCC) and those with unresectable hepatocellular carcinoma (HCC). It is also approved by the European Medicines Agency for the treatment of patients with HCC and patients with advanced RCC with whom prior IFN-α or interleukin-2-based therapy had failed or considered to be unsuitable for such therapy ("Preclinical overview of sorafenib, a multikinase inhibitor that targets both Raf and VEGF and PDGF receptor tyrosine kinase signaling". *Molecular Cancer Therapeutics* 2008; 7 (10): 3129-40).

Lapatinib, is a 4-anilinoquinazoline kinase inhibitor of the intracellular tyrosine kinase domains of both Epidermal Growth Factor Receptor (EGFR [ErbB1]) and of human Epidermal Receptor Type 2 (HER2[ErbB2]) receptors. Lapatinib inhibits ErbB-driven tumor cell growth in vitro and in various animal models. It is present as the monohydrate of the ditosylate salt, with chemical name N-(3-chloro-4-{[(3-fluorophenyl) methyl]oxy}phenyl)-6-[5-({[2-(methylsulfonyl) ethyl] amino}methyl)-2-furanyl]-4-quinazolinaminebis(4-methylbenzenesulfonate) monohydrate. Lapatinib ditosylate monohydrate is a dual tyrosine inhibitor which interrupts the HER2 growth receptor and is used in combination therapy for HER2-positive breast cancer ("Lapatinib in the treatment of breast cancer" *Expert Review of Anticancer Therapy* (Future Drugs) 7 (9): 1183-92). It is marketed under the brand name TYKERB® in the United States by GlaxoSmithKline and is available commercially. Lapatinib inhibits the tyrosine kinase activity associated with two oncogenes, EGFR (epidermal growth factor receptor) and HER2/neu (Human EGFR type 2) ("A unique structure for epidermal growth factor receptor bound to GW572016 (Lapatinib): relationships among protein conformation, inhibitor off-rate, and receptor activity in tumor cells" Cancer Res. 2004 Sep. 15; 64(18): 6652-9). Lapatinib inhibits receptor signal processes by binding to the ATP-binding pocket of the EGFR/HER2 protein kinase domain, preventing self-phosphorylation and subsequent activation of the signal mechanism ("Lapatinib: a novel dual tyrosine kinase inhibitor with activity in solid tumors". *Annals of Pharmacotherapy:* 40 (2); 261-269).

Erlotinib is an EGFR inhibitor. The drug follows gefitinib (Iress®), which was the first drug of this type. Gefitinib and erlotinib are commercially available epidermal growth factor receptor tyrosine kinase inhibitors (EGFR-TKIs) that are widely used for the treatment of non-small-cell lung cancer (NSCLC). Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor (J Clin Oncol, 2007; 25:1960-1966).

Cisplatin is a platinum compound which acts as a cytotoxic anticancer agent. This platinum-based chemotherapy drug, which kills the cancer cells by damaging DNA and inducing apoptosis. Cisplatin is commercially available for the treatment of various types of cancers, including sarcomas, some carcinomas (e.g. small cell lung cancer, and ovarian cancer), lymphomas, and germ cell tumors. Cisplatin is a non cell cycle specific cytotoxic agent which is effective against cells that are actively dividing as well as those that are merely resting before entering the cell cycle and reacts in vivo, binding to and causing cross linking of DNA which ultimately triggers apoptosis (programmed cell death).

Fluorouracil (5-FU) is an antimetabolite and a cytotoxic anti-cancer agent. 5-FU inhibits DNA synthesis and cell death and penetrates cerebrospinal fluid well. 5-FU is commercially available as an antimetabolite that interferes with RNA and DNA synthesis. 5-FU is therapeutically useful for certain types of carcinoma, such as carcinoma of the colon, rectum, breast, stomach and pancreas.

Docetaxel is an antineoplastic agent belonging to the taxoid family that acts by disrupting the microtubular network in cells that is essential for mitotic and interphase cellular functions. Docetaxel binds to free tubulin and promotes the assembly of tubulin into stable microtubules while simultaneously inhibiting their disassembly. This leads to the production of microtubule bundles without normal function and to the stabilization of microtubules, which results in the inhibition of mitosis in cells. Docetaxel's binding to microtubules does not alter the number of protofilaments in the bound microtubules, a feature which differs from most spindle poisons currently in clinical use. Docetaxel is marketed worldwide under the name Taxotere® by Sanofi—and available commercially.

Cetuximab is a recombinant, chimeric monoclonal antibody directed against the epidermal growth factor (EGFR) with antineoplastic activity. Cetuximab binds to the extracellular domain of the EGFR, thereby preventing the activation and subsequent dimerization of the receptor; the decrease in receptor activation and dimerization may result in an inhibition in signal transduction and anti-proliferative effects. This agent may inhibit EGFR-dependent primary tumor growth and metastasis. Cetuximab is commercially available as Erbitux® for treatment of metastatic colorectal cancer and head and neck cancer.

According to another embodiment, the present invention relates to a pharmaceutical combination for use in the treatment of squamous cell carcinoma of head and neck (SCCHN) wherein the combination comprises a cyclin dependent kinase (CDK) inhibitor selected from the compounds of formula I or a pharmaceutically acceptable salt or a solvate thereof and one or more of antineoplastic agents selected from sorafenib, lapatinib, erlotinib, cisplatin, 5-fluorouracil or docetaxel or a pharmaceutically acceptable salt thereof or the monoclonal antibody cetuximab.

In another embodiment, the present invention is directed to a pharmaceutical combination for use in the treatment of squamous cell carcinoma of head and neck (SCCHN) wherein the combination comprises a cyclin dependent kinase (CDK) inhibitor selected from the compounds of formula I or a pharmaceutically acceptable salt or a solvate thereof and sorafenib.

Another embodiment of the present invention provides a pharmaceutical combination for use in the treatment of squamous cell carcinoma of head and neck wherein the combination comprises a cyclin dependent kinase (CDK) inhibitor selected from the compounds of formula I or a pharmaceutically acceptable salt or a solvate thereof and lapatinib.

In another embodiment, the present invention is directed to a pharmaceutical combination for use in the treatment of squamous cell carcinoma of head and neck wherein the combination comprises a cyclin dependent kinase (CDK) inhibitor selected from the compounds of formula I or a pharmaceutically acceptable salt or a solvate thereof and erlotinib.

Another embodiment of the present invention provides a pharmaceutical combination for use in the treatment of squamous cell carcinoma of head and neck wherein the combination comprises a cyclin dependent kinase (CDK) inhibitor selected from the compounds of formula I or a pharmaceutically acceptable salt or a solvate thereof; cisplatin and 5-fluorouracil or a pharmaceutically acceptable salt thereof.

In another embodiment, the present invention is directed to a pharmaceutical combination for use in the treatment of squamous cell carcinoma of head and neck wherein the combination comprises a cyclin dependent kinase (CDK) inhibitor selected from the compounds of formula I or a pharmaceutically acceptable salt or a solvate thereof; docetaxel, cisplatin and 5-fluorouracil or a pharmaceutically acceptable salt thereof.

Further embodiment of the present invention provides a pharmaceutical combination for use in the treatment of squamous cell carcinoma of head and neck wherein the combination comprises a CDK inhibitor selected from compound A or compound B and one or more anti-neoplastic agents selected from sorafenib, lapatinib, erlotinib, cisplatin, 5-fluorouracil or docetaxel or a pharmaceutically acceptable salt thereof.

In another embodiment, the present invention provides a pharmaceutical combination for use in the treatment of squamous cell carcinoma of head and neck wherein the combination comprises compound A and sorafenib or a pharmaceutically acceptable salt thereof.

In another embodiment, the present invention is directed to a pharmaceutical combination for use in the treatment of squamous cell carcinoma of head and neck wherein the combination comprises compound A and lapatinib or a pharmaceutically acceptable salt thereof.

In another embodiment, the present invention is directed to a pharmaceutical combination for use in the treatment of squamous cell carcinoma of head and neck wherein the combination comprises compound A and erlotinib or a pharmaceutically acceptable salt thereof.

In another embodiment, the present invention is directed to pharmaceutical combination for use in the treatment of squamous cell carcinoma of head and neck wherein the combination comprises compound A, cisplatin and 5-fluorouracil or a pharmaceutically acceptable salt thereof.

Further embodiment of the present invention is directed to pharmaceutical combination for use in the treatment of squamous cell carcinoma of head and neck wherein the combination comprises compound A, docetaxel, cisplatin and 5-fluorouracil or a pharmaceutically acceptable salt thereof.

In another embodiment, the present invention is directed to a pharmaceutical combination for use in the treatment of squamous cell carcinoma of head and neck wherein the combination comprises compound B and sorafenib or a pharmaceutically acceptable salt thereof.

In another embodiment, the present invention is directed to a pharmaceutical combination for use in the treatment of squamous cell carcinoma of head and neck wherein the combination comprises the compound B and lapatinib or a pharmaceutically acceptable salt thereof.

According to another embodiment of the present invention, the pharmaceutical combination comprising the CDK inhibitor selected from the compounds of formula I and an antineoplastic agent selected from sorafenib, lapatinib or erlotinib or the pharmaceutical combination comprising the CDK inhibitor selected from the compounds of formula I, and an antineoplastic agent selected from cisplatin and 5-fluorouracil or the pharmaceutical combination comprising the CDK inhibitor selected from the compounds of formula I, and an antineoplastic agent selected from cisplatin, 5-fluorouracil and docetaxel, is not exclusively limited to those combinations which are obtained by physical association of said ingredients, but also encompass those which permit a separate administration, which can be simultaneous, sequential or spaced out over a period of time so as to obtain maximum efficacy of the combination. Thus, the pharmaceutical combination may be administered simultaneously or sequentially for an effective treatment of squamous cell carcinoma of head and neck.

According to another embodiment, the present invention is directed to a pharmaceutical combination for use in the treatment of squamous cell carcinoma comprising radiation, a CDK inhibitor selected from the compounds of formula I and one or more antineoplastic agents selected from sorafenib, lapatinib, erlotinib, cisplatin, 5-fluorouracil or docetaxel or a pharmaceutically acceptable salt thereof.

According to another embodiment, the present invention is directed to a pharmaceutical combination for use in the treatment of squamous cell carcinoma comprising radiation, a CDK inhibitor selected from compound A or compound B and one or more antineoplastic agents selected from sorafenib, lapatinib, erlotinib, cisplatin, 5-fluorouracil or docetaxel or a pharmaceutically acceptable salt thereof.

According to another embodiment, the present invention relates to a pharmaceutical combination for use in the treatment of squamous cell carcinoma of head and neck (SCCHN) wherein the combination comprises a cyclin dependent kinase (CDK) inhibitor selected from compound A or compound B, cisplatin and or a pharmaceutically acceptable salt thereof and the monoclonal antibody, cetuximab.

According to another embodiment, the present invention relates to a pharmaceutical combination for use in the treatment of squamous cell carcinoma of head and neck (SCCHN) wherein the combination comprises radiation, a cyclin dependent kinase (CDK) inhibitor selected from compound A or compound B or a pharmaceutically acceptable salt thereof and the monoclonal antibody, cetuximab.

In further embodiment, the present invention provides a pharmaceutical composition which comprises a therapeutically effective amount of a CDK inhibitor selected from the compounds of formula I (as described herein) or a pharmaceutically acceptable salt or solvate thereof in combination with a therapeutically effective amount of one or more antineoplastic agents selected from the group consisting of sorafenib, lapatinib, erlotinib, docetaxel, cisplatin and 5-fluorouracil or a pharmaceutically acceptable salt thereof; in association with a pharmaceutically acceptable carrier.

In another embodiment, the present invention relates to a pharmaceutical composition which comprises a therapeutically effective amount of a CDK inhibitor selected from the compounds of formula I or a pharmaceutically acceptable salt or solvate thereof and a therapeutically effective amount of sorafenib in association with a pharmaceutically acceptable carrier.

In another further embodiment, the present invention relates to a pharmaceutical composition which comprises a therapeutically effective amount of a CDK inhibitor selected from the compounds of formula I or a pharmaceutically acceptable salt or solvate thereof and a therapeutically effective amount of lapatinib in association with a pharmaceutically acceptable carrier.

In another further embodiment, the present invention relates to a pharmaceutical composition which comprises a therapeutically effective amount of a CDK inhibitor selected from the compounds of formula I or a pharmaceutically acceptable salt or solvate thereof and a therapeutically effective amount of erlotinib in association with a pharmaceutically acceptable carrier.

In further embodiment, the present invention provides a pharmaceutical composition which comprises a therapeutically effective amount of a CDK inhibitor selected from the compounds of formula I or a pharmaceutically acceptable salt or solvate thereof, a therapeutically effective amount of cisplatin and a therapeutically effective amount of 5-fluorouracil or a pharmaceutically acceptable salt thereof; in association with a pharmaceutically acceptable carrier.

In another embodiment, the present invention relates to a pharmaceutical composition which comprises a therapeutically effective amount of a CDK inhibitor selected from the compound A or compound B and therapeutically effective amount of one or more antineoplastic agents or a pharmaceutically acceptable salt thereof; in association with a pharmaceutically acceptable carrier.

In another embodiment, the present invention relates to a pharmaceutical composition which comprises a therapeutically effective amount of a CDK inhibitor selected from compound A or compound B and a therapeutically effective amount of one or more antineoplastic agents selected from the group consisting of sorafenib, lapatinib, erlotinib, cisplatin and 5-fluorouracil or pharmaceutically acceptable salt thereof; in association with a pharmaceutically acceptable carrier.

In another further embodiment, the present invention relates to a pharmaceutical composition which comprises a therapeutically effective amount of compound A and a therapeutically effective amount of sorafenib in association with a pharmaceutically acceptable carrier.

In another embodiment, the present invention relates to a pharmaceutical composition which comprises a therapeutically effective amount of compound A and a therapeutically effective amount of lapatinib in association with a pharmaceutically acceptable carrier.

In further embodiment, the present invention relates to a pharmaceutical composition which comprises a therapeutically effective amount of compound B and a therapeutically effective amount of sorafenib in association with a pharmaceutically acceptable carrier.

In another embodiment, the present invention relates to a pharmaceutical composition which comprises a therapeutically effective amount of compound B and a therapeutically effective amount of lapatinib in association with a pharmaceutically acceptable carrier.

In another embodiment, the present invention relates to a pharmaceutical composition which comprises a therapeutically effective amount of compound A and a therapeutically effective amount of erlotinib in association with a pharmaceutically acceptable carrier.

In another embodiment, the present invention relates to a pharmaceutical composition which comprises a therapeutically effective amount of each of the compound A, cisplatin and 5-fluorouracil or a pharmaceutically acceptable salt thereof; in association with a pharmaceutically acceptable carrier.

In another embodiment, the present invention relates to a pharmaceutical composition which comprises a therapeutically effective amount of each of the compound A, docetaxel, cisplatin and 5-fluorouracil or a pharmaceutically acceptable salt thereof; in association with a pharmaceutically acceptable carrier.

In further embodiment, the present invention is directed to a method for the treatment of squamous cell carcinoma of head and neck in a subject, which comprises administering to said subject a therapeutically effective amount of a CDK inhibitor selected from the compounds of formula (I) or a pharmaceutically acceptable salt or solvate thereof and a therapeutically effective amount of an anti-neoplastic agent selected from sorafenib, lapatinib or erlotinib; wherein said CDK inhibitor and said anti-neoplastic agent or pharmaceutically acceptable salt thereof is administered simultaneously or sequentially.

In another embodiment, the present invention is directed to a method for the treatment of squamous cell carcinoma of head and neck in a subject, which comprises administering to said subject a therapeutically effective amount of a CDK inhibitor selected from the compounds of formula (I) or a pharmaceutically acceptable salt or solvate thereof; a therapeutically effective amount of each of cisplatin and 5-fluorouracil or a pharmaceutically acceptable salt thereof; wherein said CDK inhibitor, cisplatin and 5-fluorouracil are administered simultaneously or sequentially.

In further embodiment, the present invention is directed to a method for the treatment of squamous cell carcinoma of head and neck in a subject, which comprises administering to said subject a therapeutically effective amount of a CDK inhibitor selected from the compound A or compound B and a therapeutically effective amount of antineoplastic agent selected from sorafenib, lapatinib or erlotinib; wherein compound A or compound B and antineoplastic agent is administered simultaneously or sequentially.

In another embodiment, the present invention is directed to a method for the treatment of squamous cell carcinoma of head and neck in a subject, which comprises administering to said subject a therapeutically effective amount of a CDK inhibitor selected from the compound A or compound B and a therapeutically effective amount of sorafenib; wherein said compound A or compound B and sorafenib is administered simultaneously or sequentially.

In another embodiment, the present invention is directed to a method for the treatment of squamous cell carcinoma of head and neck in a subject, which comprises administering to said subject a therapeutically effective amount of a CDK inhibitor selected from the compound A or compound B and a therapeutically effective amount of lapatinib or a pharmaceutically acceptable salt thereof; wherein said compound A or compound B and lapatinib is administered simultaneously or sequentially.

Another embodiment of the present invention provides a method for the treatment of squamous cell carcinoma of head and neck in a subject, which comprises administering to said subject a therapeutically effective amount of compound A or a pharmaceutically acceptable salt or solvate thereof and a therapeutically effective amount of erlotinib; wherein said compound A and erlotinib is administered simultaneously or sequentially.

In another embodiment, the present invention is directed to a method for the treatment of squamous cell carcinoma of head and neck in a subject, which comprises administering to said subject a therapeutically effective amount of compound A or a pharmaceutically acceptable salt or solvate thereof; a therapeutically effective amount of cisplatin and 5-fluorouracil or a pharmaceutically acceptable salt thereof; wherein said compound A, cisplatin and 5-fluorouracil are administered simultaneously or sequentially.

Another embodiment of the present invention is directed to a method for the treatment of squamous cell carcinoma of head and neck in a subject, which comprises administering to said subject a therapeutically effective amount of CDK inhibitor selected from the compounds of formula (I) or a pharmaceutically acceptable salt or solvate thereof and a therapeutically effective amount of an antineoplastic agent or a pharmaceutically acceptable salt thereof; wherein said CDK inhibitor and said anti-neoplastic agent or their pharmaceutically acceptable salts are administered sequentially.

Accordingly to another embodiment, the present invention relates to a method for the treatment of squamous cell carcinoma of head and neck in a subject comprising administering to said subject a therapeutically effective amount of compound A or compound B; a therapeutically effective amount of an antineoplastic agent selected from sorafenib, lapatinib or erlotinib; wherein said compound A or compound B and antineoplastic agent selected from sorafenib, lapatinib or erlotinib is administered sequentially such that compound A or compound B is administered before or after the administration of sorafenib or lapatinib or erlotinib.

Accordingly to another embodiment, the present invention relates to a method for the treatment of squamous cell carcinoma of head and neck in a subject comprising administering to said subject a therapeutically effective amount of compound A and a therapeutically effective amount of sorafenib; wherein said compound A and sorafenib is administered sequentially such that compound A is administered before or after the administration of sorafenib.

Accordingly to another embodiment, the present invention relates to a method for the treatment of squamous cell carcinoma of head and neck in a subject comprising administering to said subject a therapeutically effective amount of compound B and a therapeutically effective amount of sorafenib; wherein said compound B and sorafenib is administered sequentially such that compound B is administered before or after the administration of sorafenib.

Accordingly to another embodiment, the present invention relates to a method for the treatment of squamous cell carcinoma of head and neck in a subject comprising administering to said subject a therapeutically effective amount of compound A and a therapeutically effective amount of lapatinib; wherein said compound A and lapatinib is administered sequentially such that compound A is administered before or after the administration of lapatinib.

Accordingly to another embodiment, the present invention relates to a method for the treatment of squamous cell carcinoma of head and neck in a subject comprising administering to said subject a therapeutically effective amount of compound B and a therapeutically effective amount of lapatinib; wherein said compound B and lapatinib is administered sequentially such that compound B is administered before or after the administration of lapatinib.

Accordingly to another embodiment, the present invention relates to a method for the treatment of squamous cell carcinoma of head and neck in a subject comprising administering to said subject a therapeutically effective amount of compound A; a therapeutically effective amount of erlotinib; wherein said compound A and erlotinib is administered sequentially such that compound A is administered before or after the administration of erlotinib.

Accordingly to another embodiment, the present invention relates to a method for the treatment of squamous cell carcinoma of head and neck in a subject comprising administering to said subject a therapeutically effective amount of compound A; a therapeutically effective amount of each of cisplatin; and 5-fluorouracil or a pharmaceutically acceptable salt thereof; wherein said compound A, cisplatin and 5-fluorouracil or a pharmaceutically acceptable salt thereof are administered sequentially such that compound A is administered before or after the administration of cisplatin and/or 5-fluorouracil.

Accordingly to another embodiment, the present invention relates to a method for the treatment of squamous cell carcinoma of head and neck in a subject comprising administering to said subject a therapeutically effective amount of compound A; a therapeutically effective amount of each of docetaxel; cisplatin and 5-fluorouracil or a pharmaceutically acceptable salt thereof; wherein said compound A, docetaxel, cisplatin and 5-fluorouracil or a pharmaceutically acceptable salt thereof are administered sequentially such that compound A is administered before or after the administration of docetaxel, and/or cisplatin and/or 5-fluorouracil.

In another embodiment the present invention provides use of combination of a CDK inhibitor selected from the compound of formula I or pharmaceutically acceptable salt or solvate thereof and one or more antineoplastic agents or a pharmaceutically acceptable salt thereof for the manufacture of a medicament for the treatment or prevention of squamous cell carcinoma of the head and neck (SCCHN).

Another embodiment of the present invention provides use of pharmaceutical composition comprising a therapeutically effective amount of CDK inhibitor selected from the compounds of formula (I) or a pharmaceutically acceptable salt thereof and an antineoplastic agent for the manufacture of a medicament for the treatment of squamous cell carcinoma of the head and neck (SCCHN).

According to the present invention the administration of the double combination of CDK inhibitor selected from the compound of formula I and an antineoplastic agent or a pharmaceutically acceptable salt thereof selected from sorafenib, lapatinib or erlotinib may produce effects, such as the anti-cancer effects, greater than those achieved with any of the CDK inhibitor or sorafenib or lapatinib or erlotinib when used alone.

It is further provided by the present invention that the administration of a triple combination of the CDK inhibitor selected from the compound of formula I as described herein, cisplatin and 5-fluorouracil may produce effects, such as anti-cancer effects, greater than those achieved with any of the CDK inhibitor or cisplatin or 5-fluorouracil used alone, greater than those achieved with the combination of the CDK inhibitor, cisplatin and 5-fluorouracil.

The administration route of the pharmaceutical composition of the present invention is not particularly limited. In one embodiment, the active ingredients (the anticancer agents contained in the combination) comprised in the composition may have to be administered by different routes either orally or parenterally depending on the dosage form. The dosage form suitable for oral administration may be a tablet or capsule, forms of parenteral administration include intravenous injection, intravenous infusion, subcutaneous injection, transdermal injection, intraperitoneal injection and so on. For rectal administration, for example as a suppository or the route of administration may be by direct injection into the tumour or by regional delivery or by local delivery. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc and sugar. For, intramuscular, intraperitoneal, subcutaneous and intravenous use, sterile solutions of the active ingredient are usually employed, and the pH of the solutions should be suitably adjusted and buffered.

In practice of the present invention, CDK inhibitors selected from the compounds of Formula I may be administered either orally or parenterally to generate and maintain good blood levels thereof, while one or more antineoplastic agents may be administered orally or parenterally, by intravenous, subcutaneous or intramuscular route or any other suitable route of administration.

In one embodiment, the therapeutic agents (the CDK inhibitors and the antineoplastic agents) contained in the combination of the invention are formulated in accordance with routine procedures as a pharmaceutical composition.

In practice, oral preparations for oral administration may be produced by adding to the active ingredients fillers, and if necessary, binders, disintegrants, lubricants, coloring agents, flavoring agents, etc. and formulating the resultant mixture according to conventional procedures into tablets, coated tablets, granules, subtle granules, powders, capsules or the like. Examples of the filler include but not limited to lactose, corn starch, white sugar, glucose, sorbitol, crystalline cellulose, silicon dioxide, etc. Examples of the binder include but not limited to polyvinyl alcohol, ethylcellulose, methylcellulose, gum arabic, hydroxypropyl cellulose, hydroxypropyl methylcellulose, etc. Examples of the lubricant include but not limited to magnesium stearate, talc, silica, etc. The coloring agent may be any coloring agent which is approved to be added to pharmaceutical preparations. Examples of the flavoring agent include but not limited to cocoa powder, menthol, aromatic powder, peppermint oil, camphol, cinnamon powder, etc. Resultant tablets and granules may be appropriately coated with, for example, sugar or gelatin according to necessity. When the pharmaceutical composition of the present invention is administered transdermally in the form of patch, it is preferable to select the so-called free-form that does not form a salt. Injection preparations may be produced as intravenous infusion preparations or intravenous, subcutaneous or intramuscular injection preparations according to conventional procedures. Examples of the suspending agent include but not limited to methylcellulose, polysolvate 80, hydroxyethyl cellulose, gum arabic, powdered tragacanth, sodium carboxymethylcellulose, polyoxyethylene sorbitan monolaurate, etc. Examples of the dissolution aid include but not limited to polyoxyethylene hydrogenated castor oil, polysolvate 80, nicotinamide, polyoxyethylene sorbitan monolaurate, macrogol, fatty acid ethyl ester from castor oil, etc. Examples of the stabilizer include but not limited to sodium sulfite, sodium metasulfite, etc. Examples of the preservative include methyl parahydroxybenzoate, ethyl parahydroxybenzoate, sorbic acid, phenol, cresol, chlorocresol etc.

Although the effective doses of therapeutic agents (the CDK inhibitors and the antineoplastic or anticancer agents) for administration vary depending on the severity of symptom, the age, sex, body weight and sensitivity difference of the patient, the mode, time, interval and duration of administration, the nature, formulation and type of the preparation, the type of the active ingredient, etc. In certain embodiments, the therapeutic agents are administered in a time frame where both agents are still active. One skilled in the art would be able to determine such a time frame by determining the half life of the administered therapeutic agents. As indicated herein before, the active ingredients contained in the pharmaceutical composition can be administered simultaneously or sequentially. Those skilled in the art will recognize that several variations are possible within the scope and spirit of this invention.

For effective administration, the therapeutic agents of the pharmaceutical combination of the present invention are provided in a particular dose range, for example the CDK inhibitor selected from compound of formula I such as the compound A may be provided in a general dose range of 75 mg/m$^2$/day to 200 mg/m$^2$/day; another CDK inhibitor selected from compound of formula I such as the Compound B may be provided in a general dose range of 50 mg to 350 mg orally. Further, among the antineoplastic agents, cisplatin may be provided in a dose range of 40 mg/m$^2$/day to 200 mg/m$^2$/day, 5-fluorouracil may be provided in dose range of 40 mg/m$^2$/day to 200 mg/m$^2$/day, docetaxel may be provided in a general dose range of 20 mg/m$^2$/day to 75 mg/m$^2$/day, sorafenib may be provided in at least an amount from about 200 mg to 400 mg (2×200 mg tablet) PO bid (orally twice a day), lapatinib may be provided in a dose ranging from 500 to 1500 mg/d and erlotinib may be provided in a dose range of about 150 mg/day to 300 mg/day.

In a further embodiment, the present invention provides a kit comprising a therapeutically effective amount of a CDK inhibitor selected from the compound of formula I or a pharmaceutically acceptable salt thereof in combination with one or more antineoplastic agents selected from sorafenib, lapatinib, erlotinib, cisplatin and 5-fluorouracil or a pharmaceutically acceptable salt thereof.

The combinations provided by this invention have been evaluated in certain assay systems, the experimental details are as provided herein below.

The synergistic efficacy of the combination of present invention is demonstrated by conducting the in vitro study involving use of a combination for example a CDK inhibitor of formula I as described herein as compound A or compound B and one or more antineoplastic agents selected from sorafenib, lapatinib, erlotinib, cisplatin, 5-fluorouracil or docetaxel. It is clearly indicated that the antineoplastic agents when used in combination with CDK inhibitors in the treatment of squamous cell carcinoma of head and neck the apoptosis in proliferative cells increases than when the cells are treated with the CDK inhibitor of formula I alone or antineoplastic agent alone. For instance, it is clearly established from the data described herein that the CDK inhibitor of formula I, compound described herein as the compound A or compound B in combination with one or more antineoplastic agents selected from sorafenib, lapatinib, erlotinib, cisplatin, 5-fluorouracil or docetaxel, are synergistically effective in the treatment of squamous cell carcinoma of the head and neck. The synergism exhibited by the pharmaceutical combination of the present invention is also demonstrated through in vivo study data as indicated herein.

It is understood that modifications that do not substantially affect the activity of the various embodiments of this invention are included within the invention disclosed herein. Accordingly, the following examples are intended to illustrate but not to limit the present invention.

Example 1

A) General Procedure for the Preparation of the CDK Inhibitors (the Compounds of Formula I)

The compounds of formula I may be prepared according to the methods disclosed in PCT Patent Publication No. WO2004004632 and PCT Patent Publication No. WO2007148158 which are incorporated herein by reference.

The general process for the preparation of the compound of formula I, or a pharmaceutically acceptable salt thereof, comprises the following steps:

a) treating the resolved enantiomerically pure (−)-trans enantiomer of the
   intermediate compound of formula VIA,

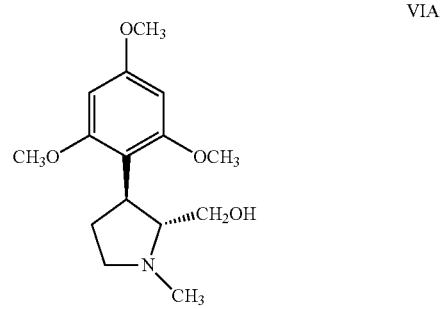

VIA with acetic anhydride in the presence of a Lewis acid catalyst to obtain a resolved acetylated compound of formula VIIA,

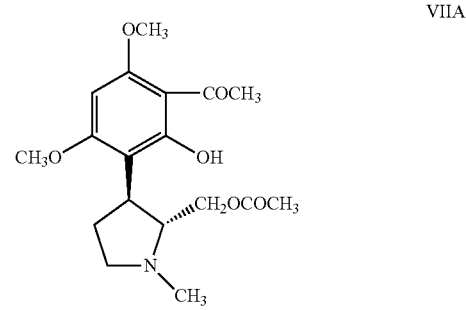

VIIA b) reacting the resolved acetylated compound of formula VIIA with an acid of formula ArCOOH or an acid chloride of formula ArOOCl or an acid anhydride of formula (ArCO)$_2$O or an ester of formula ArCOOCH$_3$, wherein Ar is as defined hereinabove in reference to the compound of formula I, in the presence of a base and a solvent to obtain a resolved compound of formula VIIIA;

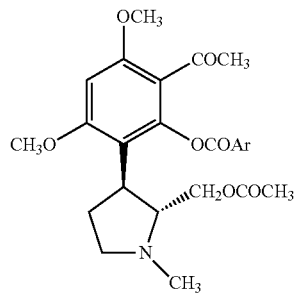

c) treating the resolved compound of formula VIIIA with a base in a suitable solvent to obtain the corresponding resolved β-diketone compound of formula IXA;

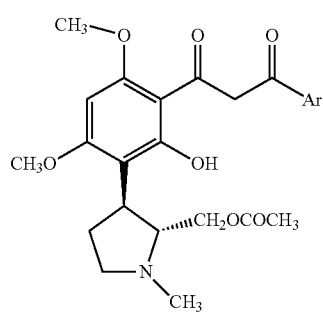

wherein Ar is as defined above;

d) treating the resolved β-diketone compound of formula IXA with an acid such as hydrochloric acid to obtain the corresponding cyclized compound of formula XA,

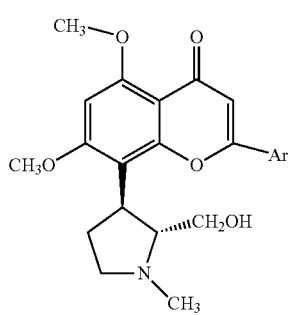

e) subjecting the compound of formula XA to dealkylation by heating it with a dealkylating agent at a temperature ranging from 120-180° C. to obtain the (+)-trans enantiomer of the compound of formula I and, optionally, converting the subject compound into its pharmaceutically acceptable salt.

The Lewis acid catalyst utilized in the step (a) above may be selected from: $BF_3$, $Et_2O$, zinc chloride, aluminium chloride and titanium chloride.

The base utilized in the process step (b) may be selected from triethylamine, pyridine and a DCC-DMAP combination (combination of N, N'-dicyclohexyl carbodiimide and 4-dimethylaminopyridine).

It will be apparent to those skilled in the art that the rearrangement of the compound of formula VIIIA to the corresponding β-diketone compound of formula IXA is known as a Baker-Venkataraman rearrangement (J. Chem. Soc., 1381 (1933) and Curr. Sci., 4,214 (1933)).

The base used in the process step (c) may be selected from: lithium hexamethyl disilazide, sodium hexamethyldisilazide, potassium hexamethyldisilazide, sodium hydride and potassium hydride. A preferred base is lithium hexamethyl disilazide.

The dealkylating agent used in process step (e) for the dealkylation of the compound of formula IXA may be selected from: pyridine hydrochloride, boron tribromide, boron trifluoride etherate and aluminium trichloride. A preferred dealkylating agent is pyridine hydrochloride.

Preparation of the starting compound of formula VIA involves reacting 1-methyl-4-piperidone with a solution of 1,3,5-trimethoxybenzene in glacial acetic acid, to yield 1-methyl-4-(2,4,6-trimethoxyphenyl)-1,2,3,6-tetrahydropyridine, which is reacted with boron trifluoride diethyl etherate, sodium borohydride and tetrahydrofuran to yield 1-methyl-4-(2,4,6-trimethoxyphenyl)piperidin-3-ol. Conversion of 1-methyl-4-(2,4,6-trimethoxyphenyl)piperidin-3-ol to the compound of formula VIA involves converting the hydroxyl group present on the piperidine ring of the compound, 1-methyl-4-(2,4,6-trimethoxyphenyl)piperidin-3-ol to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol.

B) Preparation of (+)-trans-2-(2-Chloro-phenyl)-5,7-dihydroxy-8-(2-hydroxymethyl-1-methyl-pyrrolidin-3-yl)-chromen-4-one hydrochloride (compound A)

Molten pyridine hydrochloride (4.1 g, 35.6 mmol) was added to (+)-trans-2-(2-chloro-phenyl)-8-(2-hydroxymethyl-1-methyl-pyrrolidin-3-yl)-5,7-dimethoxy-chromen-4-one (0.4 g, 0.9 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (5 mL), stirred for 30 min., filtered and dried to obtain the compound, (+)-trans-2-(2-chloro-phenyl)-5,7-dihydroxy-8-(2-hydroxymethyl-1-methyl-pyrrolidin-3-yl)-chromen-4-one.

Yield: 0.25 g (70%); IR (KBr): 3422, 3135, 1664, 1623, 1559 cm-1;

1H NMR (CDCl3, 300 MHz): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H); MS (ES+): m/z 402 (M+1);

Analysis: $C_{21}H_{20}ClNO_5$ C, 62.24 (62.71); H, 5.07 (4.97); N, 3.60 (3.48); Cl, 9.01 (8.83).

The compound as obtained above (0.2 g, 0.48 mmol) was suspended in IPA (5 mL) and 3.5% HCl (25 ml) was added. The suspension was heated to get a clear solution. The solution was cooled and solid filtered to obtain the compound, (+)-trans-2-(2-Chlorophenyl)-5,7-dihydroxy-8-(2-hydroxymethyl-1-methyl-pyrrolidin-3-yl)-chromen-4-one hydrochloride.

Yield: 0.21 g (97%); mp: 188-192° C.; [α]D25=+21.3° (c=0.2, methanol);

1H NMR (CD3OD, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H); MS (ES+): m/z 402 (M+1)(free base).

This compound was subjected to chiral HPLC. Chiral HPLC was done using column Chiralcel OD-H (250×4.6 mm) and solvent system haxane:ethanol (92:08) with TFA (0.4%). The results are recorded at 264 nm with solvent flow rate of 1 mL/min. As depicted in the chiral HPLC showed 100% e.e of the compound, (+)-trans-2-(2-chloro-phenyl)-5,7-dihydroxy-8-(2-hydroxy-methyl-1-methyl-pyrrolidin-3-yl)-chromen-4-one hydrochloride.

C) Preparation of (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride (Compound B)

A mixture of the compound, (+)-trans-2-(2-Chloro-4-trifluoromethylphenyl)-8-(2-hydroxymethyl-1-methyl pyrrolidin-3-yl)-5,7-dimethoxy-chromen-4-one (0.25 g, 0.5 mmol), pyridine hydrochloride (0.25 g, 2.16 mmol) and a catalytic amount of quinoline was heated at 180° C. for a period of 2.5 hrs. The reaction mixture was diluted with methanol (25 ml) and basified with solid $Na_2CO_3$ to pH 10. The reaction mixture was filtered, and washed with methanol. The organic layer was concentrated and the residue purified by column chromatography using 0.1% ammonia and 4.5% methanol in chloroform as eluent to yield the compound, (+)-trans-2-(2-chloro-4-trifluoromethylphenyl)-5,7-dihydroxy-8-(2-hydroxy-methyl-1-methylpyrrolidin-3-yl)-chromen-4-one, as a yellow solid.

Yield: 0.15 g (63.7%);

1H NMR (CDCl3, 300 MHz): δ 7.99 (m, 2H), 7.83 (d, 1H), 6.65 (s, 1H), 6.41 (s, 1H), 4.24 (m, 1H), 3.90 (m, 2H), 3.70 (m, 1H), 3.60 (m, 1H), 3.41 (m, 1H), 2.99 (s, 3H), 2.54 (m, 1H), 2.28 (m, 1H); MS (ES+): m/z 470 (M+1).

The compound (0.1 g, 0.2 mmol) as obtained above was suspended in methanol (2 mL) and treated with ethereal HCl and the organic solvent evaporated to yield the compound, (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride.

Yield: 0.1 g (92.8%);

1H NMR (CDCl3, 300 MHz): δ 8.02 (d, 2H), 7.83 (d, 1H), 6.64 (s, 1H), 6.41 (s, 1H), 4.23 (m, 1H), 3.73 (m, 2H), 3.68 (m, 1H), 3.51 (m, 1H), 3.39 (m, 1H), 2.99 (s, 3H), 2.54 (m, 1H), 2.31 (m, 1H).

In Vitro Studies Involving Use of the Combination Consisting of a CDK Inhibitor and One or More Antineoplastic Agents In vitro studies involving use of a combination comprising a CDK inhibitor selected from (+)-trans-2-(2-Chloro-phenyl)-5,7-dihydroxy-8-(2-hydroxymethyl-1-methyl-pyrrolidin-3-yl)-chromen-4-one hydrochloride (compound A) and (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride (compound B) and one or more anti-neoplastic agents selected from sorafenib, lapatinib, erlotinib, docetaxel, cisplatin or 5-fluorouracil, exhibiting the synergistic effect of the combination of the present invention are illustrated in the following examples.

Example 2

Materials:

Sorafenib, lapatinib and erlotinib were obtained from LC Labs (USA). Cisplatin, 5-fluorouracil and docetaxel were obtained from Sigma. CK-8 cytotoxicity kit was procured from Dojindo Molecular Technologies, Japan. Culture media and fetal bovine serum (FBS) were obtained from Sigma (St. Louis, Mo.) and Gibco (Paisley, Scotland) respectively. The head and neck cancer cells SCC-25, Detroit 562, and FADU were obtained from the American Type Culture Collection (ATCC, Manassas, Va.). Cells were maintained in Dulbecco's Modified Eagle Medium (DMEM), supplemented with 10% FBS, Penicillin-Streptomycin Solution Stabilized, sterile-filtered, with 100 units penicilin/ml and 100 mg streptomycin/ml. The cells were grown in 75-$cm^2$ culture flasks and kept in a humidified (37° C., 5% $CO_2$) incubator.

Cells were passaged on reaching 80% confluence.

Cell Proliferation Assay:

Logarithmically growing cells were plated at a density of $3×10^3$ cells/well and allowed to recover overnight. The cells were challenged with varying concentration of different anticancer agents (compound A, compound B, sorafenib, lapatinib erlotinib, cisplatin, docetaxel and 5-fluorouracil) and the control cells received standard media containing dimethyl sulfoxide (DMSO) vehicle at a concentration of 0.2%. After 72 hours, cell toxicity was determined by CCK-8 (Cell Counting Kit-8) reagent (Dojindo Molecular Technologies, Japan); WST-8 (2-(2-methoxy-4-nitrophenyl)-3-(4-nitrophenyl)-5-(2, 4-disulfophenyl)]-2H-tetrazolium, monosodium salt) assay. In accordance with the manufacturer's instructions, 5 μl/well CCK-8 reagent was added and plates were incubated for 2 hours. The toxicity was determined by measuring the absorbance on Tecan Sapphire multi-fluorescence micro-plate reader (Tecan, Germany, GmbH) at a wavelength of 450 nm corrected to 650 nm and normalized to controls.

A CCK-8 non-radioactive colorimetric assay was carried out to characterize the in vitro growth of SCC-25, Detroit 562, and FADU as well as to test the anti-proliferative/cytotoxic activity of the anticancer agents, compound A, compound B, sorafenib, lapatinib, erlotinib, cisplatin, docetaxel and 5-fluorouracil when used in combination. CCK-8 allows convenient assays using Dojindo's tetrazolium salt, WST [8[(2-(2-methoxy-4-nitrophenyl)-3-(4-nitrophenyl)-5-(2,4-disulfophenyl)-2H-tetrazolium, monosodium salt], which produces a water-soluble formazan dye upon bioreduction in the presence of an electron carrier, 1-Methoxy PMS. CCK-8 solution is added directly to the cells; no pre-mixing of components is required. CCK-8 is a sensitive nonradioactive colorimetric assay for determining the number of viable cells in cell proliferation and cytotoxicity assays. WST-8 is bio-reduced by cellular dehydrogenases to an orange formazan product that is soluble in tissue culture medium. The amount of formazan produced is directly proportional to the number of living cells. The detection sensitivity of cell proliferation assays using WST-8 is higher than assays using the other tetrazolium salts such as MIT, XTT, MTS or WST-1. Optical Density was determined at measurement wavelength of 450 nm and reference wave length of 630 nm.

Determination of 50 Percent Inhibitory Concentrations ($IC_{50}$) of the Compound A, Compound B, Sorafenib, Lapatinib, Erlotinib, Docetaxel, Cisplatin and 5-FU.

In order to determine the $IC_{50}$ of compound A, compound B, sorafenib and lapatinib, in SCC-25, Detroit 562 and FADU cells and $IC_{50}$ of erlotinib, docetaxel, cisplatin and 5-FU in Detroit 562 and FADU cells, the cells were treated with the specified anticancer agents ("the test compounds") at the below mentioned concentrations. All the anticancer agents in the following doses of final concentration 0.03 µM, 0.1 µM, 0.3 µM, 1 µM, 3 µM, 10 µM, 30 µM and 100 µM were analyzed for their capacity to exhibit cytotoxicity particularly to exhibit 50% cytotoxicity. The cells were seeded at a density of 3000 cells/well, in a 200 µL in tissue culture grade 96 well plate and were allowed to recover for 24 hrs in a humidified 5%±0.2 $CO_2$ incubator at 37° C.±0.5° C. After 24 hrs, 1 µL of 200× (200 times higher than required concentration is denoted as 200×) test compound (compound A, compound B lapatinib, sorafenib, erlotinib, docetaxel, cisplatin and 5-fluorouracil) dissolved in neat dimethyl sulfoxide (DMSO) was added to the cells. The final DMSO concentration was 0.5% in wells. Plates were incubated for 48 hrs in humidified 5%±0.2 $CO_2$ incubator at 37±0.5° C. After 48 hrs the plates were removed from $CO_2$ incubator and 5 µL of Cell counting Kit (CCK-8) per well was added. The same plate was kept at 37° C. for 3 hrs, and allowed to come to room temperature. The absorbance at a wavelength of 450 nm was read on Tecan safire reader. The percent cytotoxicity was calculated using the following formula.

$$\text{Percent Cytotoxicity} = \frac{(OD \text{ of Control} - OD \text{ Treated cells} \times 100)}{OD \text{ DMSO control}}$$

Figure 1B:
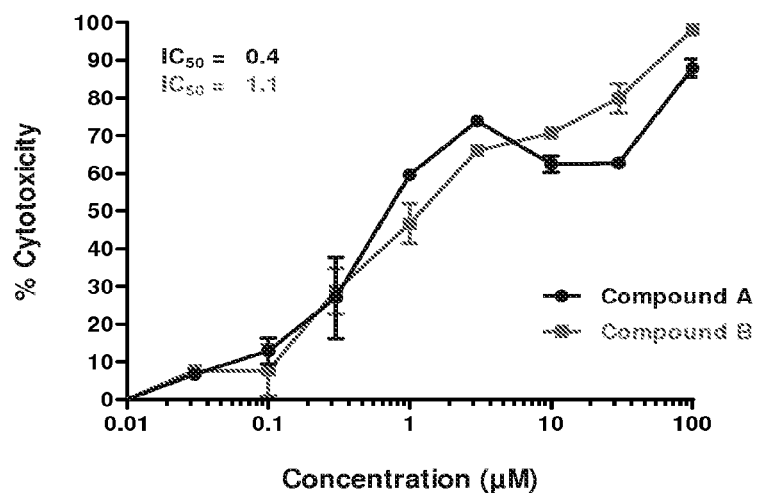
FIG. 1b is a graphical representation of the percentage inhibition results of dosing of compound A and compound B in SCC25 cells.

Dose response studies at 72 hr in SCC-25 cells showed that the Compound A, Compound B, sorafenib and lapatinib inhibited 50% growth ($IC_{50}$) at 0.4 µM, 1.1 µM, 2.7 µM and 0.5 µM respectively. The results are presented in Table 1 and are graphically presented in FIGS. 1a and 1b.

Figure 2A:
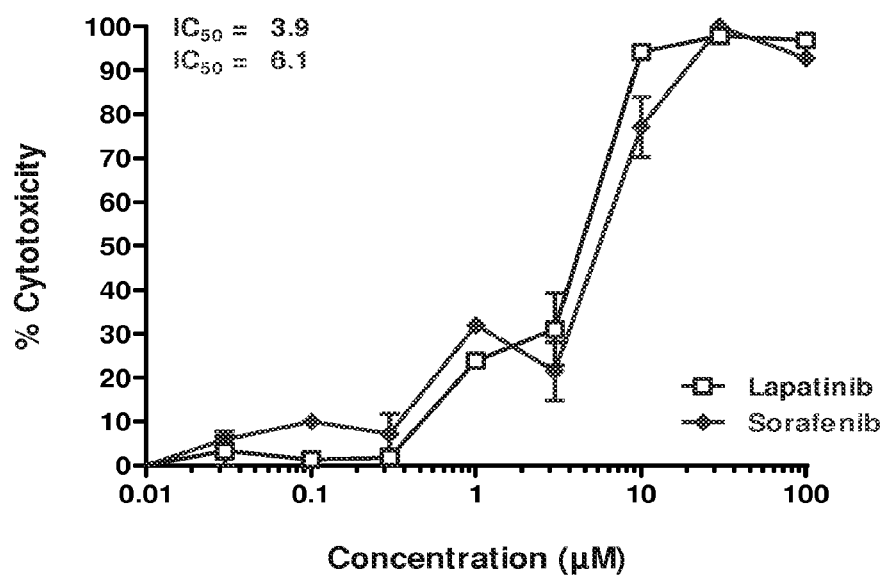
FIG. 2a is a graphical representation of the percentage inhibition results of dosing of sorafenib and lapatinib in Detroit-562 cells
Figure 2B:
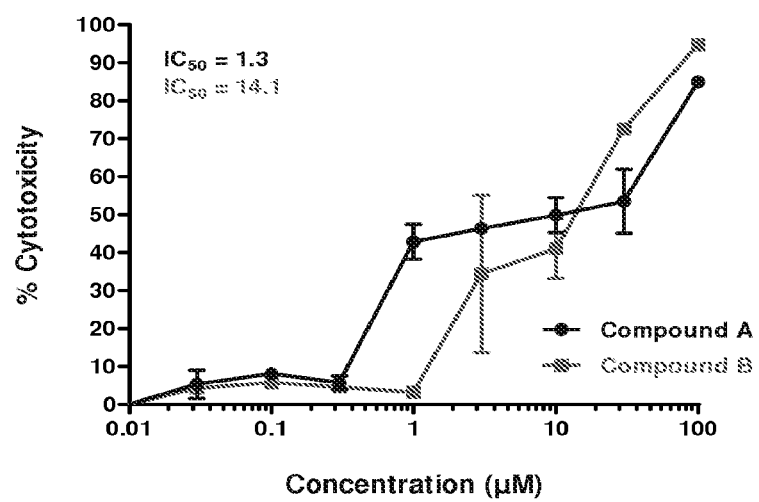
FIG. 2b is a graphical representation of the percentage inhibition results of dosing of compound A and compound B in Detroit-562 cells.

Dose response studies at 72 hr in Detroit-562 cells showed that the Compound A, Compound B, sorafenib and lapatinib inhibited 50% growth ($IC_{50}$) at 1.3 µM, 14.1 µM, 6.1 µM and 3.9 µM respectively. The results are presented in Table 2 and are graphically presented in FIGS. 2a and 2b.

Figure 3A:
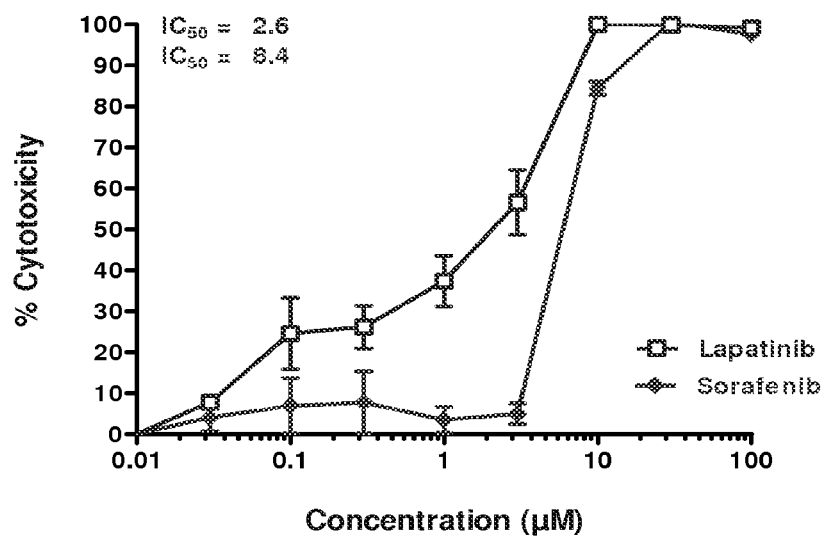
FIG. 3a is a graphical representation of the percentage inhibition results of dosing of sorafenib and lapatinib in FADU cells.
Figure 3B:
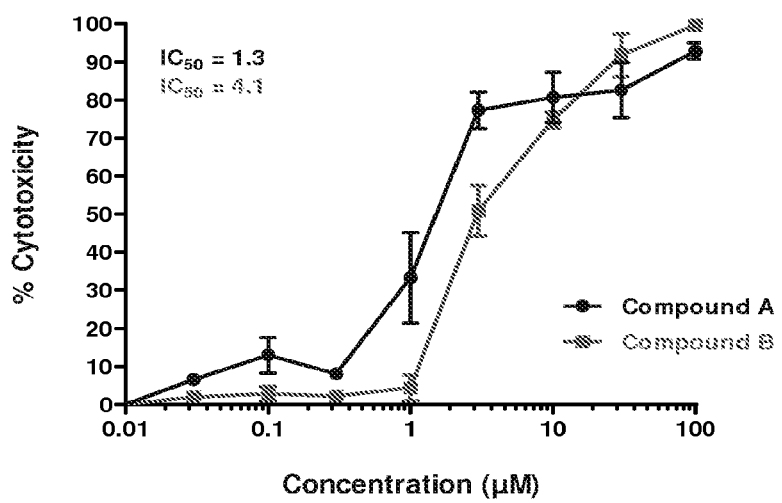
FIG. 3b is a graphical representation of the percentage inhibition results of dosing of compound A and compound B in FADU cells.

Dose response studies at 72 hr in FADU cells showed that compound A, compound B, sorafenib and lapatinib inhibited 50% growth ($IC_{50}$) at 1.3 µM, 4.1 µM, 8.4 µM and 2.6 µM respectively. The results are presented in Table 3 and are graphically presented in FIGS. 3a and 3b.

Figure 4A:
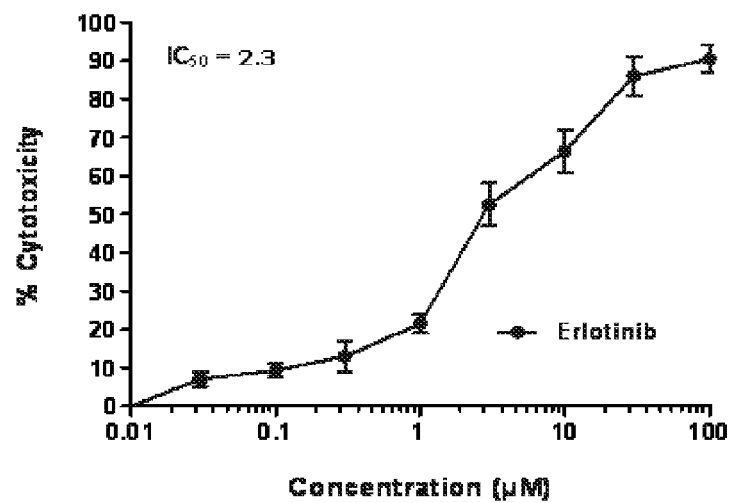
FIG. 4a is a graphical representation of the percentage inhibition results of dosing of erlotinib in Detroit-562 cells.

Dose-response studies at 72 hr in Detroit-562 cells showed that compound A and erlotinib inhibited 50% growth ($IC_{50}$) at 1.3 µM, and 2.3 µM respectively. The results are presented in Table 4 and are graphically presented in FIG. 4a.

Figure 4B:
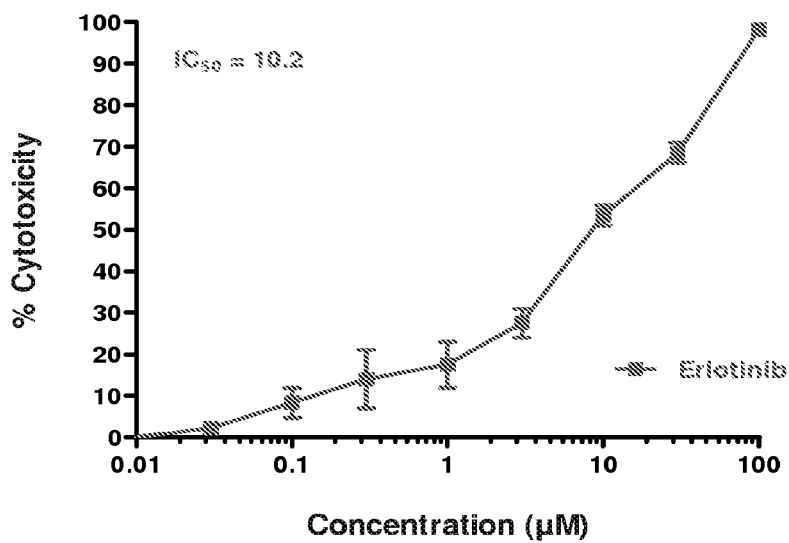
FIG. 4b is a graphical representation of the percentage inhibition results of dosing of erlotinib in FADU cells.

Dose-response studies at 72 hr in FADU cells showed that the compound A and erlotinib inhibited 50% growth ($IC_{50}$) at 1.3 µM, and 10.2 µM respectively. The results are presented in Table 5 and are graphically presented in FIG. 4b.

Figure 5A:
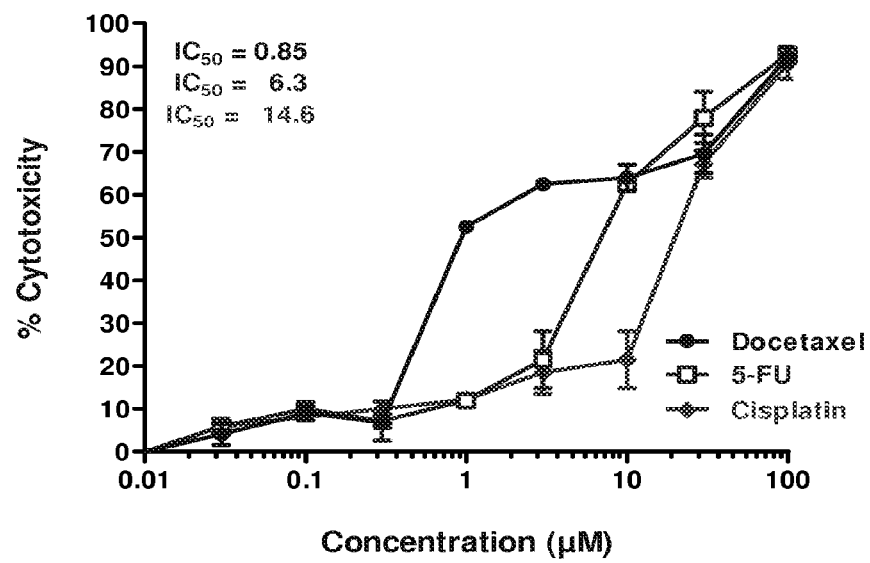
FIG. 5a is a graphical representation of the percentage inhibition results of dosing of cisplatin, 5-fluorouracil and docetaxel in Detroit-562 cells.

Dose-response studies at 72 hr in Detroit-562 cells showed that cisplatin, compound A and 5-FU inhibited 50% growth ($IC_{50}$) at 14.6 µM, 1.3 µM, and 6.3 µM respectively. The results are presented in Table 6 and are graphically represented in FIG. 5a.

Figure 5B:
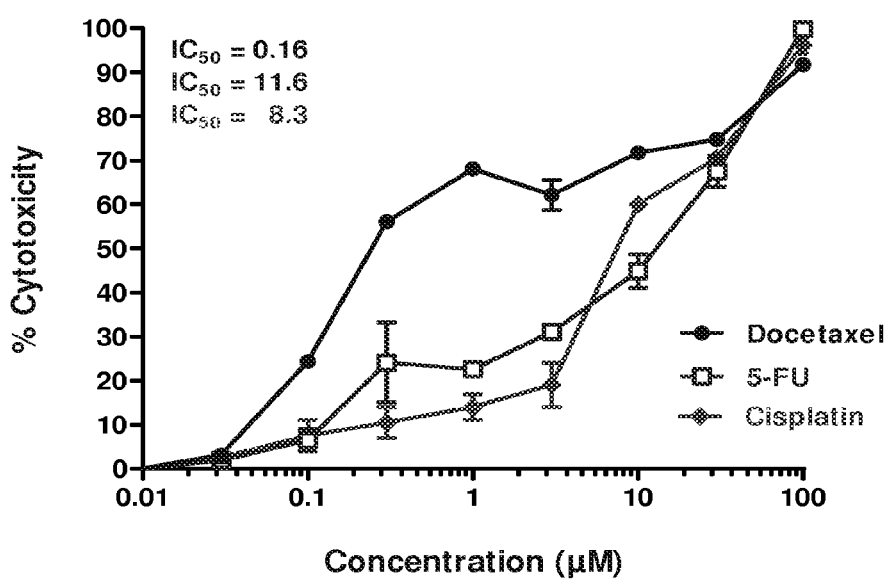
FIG. 5b is a graphical representation of the percentage inhibition results of dosing of cisplatin, 5-fluorouracil and docetaxel in FADU cells.

Dose-response studies at 72 hr in FADU cells showed that the cisplatin, compound A and 5-FU inhibited 50% growth ($IC_{50}$) at 8.3 µM, 1.3 µM, and 11.6 µM respectively. The results are presented in Table 7 and are graphically represented in FIG. 5b.

Dose-response studies at 72 hr in Detroit-562 cells showed that docetaxel, cisplatin, compound A and 5-FU inhibited 10% growth ($IC_{10}$) at 0.009 µM, 0.3 µM, 0.1 µM and 0.31 µM and 50% growth ($IC_{50}$) at 0.85 µM, 14.6 µM, 1.3 µM, and 6.3 µM respectively. The results are presented in Table 6 and are graphically represented in FIG. 5a.

Dose-response studies at 72 hr in FADU cells showed that docetaxel, cisplatin, compound A and 5-FU inhibited 10% growth ($IC_{10}$) at 0.003 µM, 0.25 µM, 0.08 µM, and 0.31 µM and 50% growth ($IC_{50}$) at 0.16 µM, 8.3 µM, 1.3 µM, and 11.6 µM respectively. The results are presented in Table 7 and are graphically represented in FIG. 5b.

Similarly the $IC_{30}$, $IC_{70}$ and $IC_{90}$ concentrations for all the tested compounds (anticancer compounds) were established from dose in which particular compound shows 30%, 70% and 90% activity respectively in the cytotoxicity assay.

TABLE 1

30%, 50%, 70% and 90% inhibitory concentrations ($IC_{30}$, $IC_{50}$, $IC_{70}$ and $IC_{90}$) of compound A, compound B, sorafenib and lapatinib in SCC-25 cells.

| Anti-cancer agent | SCC-25 cells (Inhibitory conc. in µM) | | | |
| --- | --- | --- | --- | --- |
| | $IC_{30}$ | $IC_{50}$ | $IC_{70}$ | $IC_{90}$ |
| Compound A | 0.1 | 0.4 | 4.1 | 33.3 |
| Compound B | 0.2 | 1.1 | 4.8 | 41.8 |
| Sorafenib | 0.18 | 2.7 | 6.8 | 11.7 |
| Lapatinib | 0.2 | 0.5 | 3.3 | 9.9 |

TABLE 2

30%, 50%, 70% and 90% inhibitory concentrations ($IC_{30}$, $IC_{50}$, $IC_{70}$ and $IC_{90}$) of compound A, compound B, sorafenib and lapatinib in Detroit-562 cells.

| Anti-cancer agent | Detroit-562 cells (Inhibitory conc. in µM) | | | |
| --- | --- | --- | --- | --- |
| | $IC_{30}$ | $IC_{50}$ | $IC_{70}$ | $IC_{90}$ |
| Compound A | 0.5 | 1.3 | 12.1 | 26.3 |
| Compound B | 2.7 | 14.1 | 25.2 | 44.6 |
| Sorafenib | 1.8 | 6.1 | 11.2 | 15.3 |
| Lapatinib | 1.0 | 3.9 | 7.6 | 12.6 |

TABLE 3

30%, 50%, 70% and 90% inhibitory concentrations ($IC_{30}$, $IC_{50}$, $IC_{70}$ and $IC_{90}$) of compound A, compound B, sorafenib and lapatinib in FADU cells.

| Anti-cancer agent | FADU cells (Inhibitory conc. in µM) | | | |
| --- | --- | --- | --- | --- |
| | $IC_{30}$ | $IC_{50}$ | $IC_{70}$ | $IC_{90}$ |
| Compound A | 0.2 | 1.3 | 8.3 | 28.3 |
| Compound B | 2.3 | 4.1 | 9.6 | 31.4 |
| Sorafenib | 3.9 | 8.4 | 14.8 | 30.6 |
| Lapatinib | 0.8 | 2.6 | 8.7 | 14.3 |

TABLE 4

30%, 50%, 70% and 90% inhibitory concentrations ($IC_{30}$, $IC_{50}$, $IC_{70}$ and $IC_{90}$) of compound A and erlotinib in Detroit-562 cells.

| Anti-cancer agent | Detroit-562 cells (Inhibitory conc. In µM) | | | |
|---|---|---|---|---|
| | $IC_{30}$ | $IC_{50}$ | $IC_{70}$ | $IC_{90}$ |
| Compound A | 0.5 | 1.3 | 12.1 | 26.3 |
| Erlotinib | 1.4 | 2.3 | 6.3 | 10.7 |

TABLE 5

30%, 50%, 70% and 90% inhibitory concentrations ($IC_{30}$, $IC_{50}$, $IC_{70}$ and $IC_{90}$) of compound A and erlotinib in FADU cells.

| Anti-cancer agent | FADU cells (Inhibitory conc. In µM) | | | |
|---|---|---|---|---|
| | $IC_{30}$ | $IC_{50}$ | $IC_{70}$ | $IC_{90}$ |
| Compound A | 0.2 | 1.3 | 8.3 | 28.3 |
| Erlotinib | 0.9 | 10.2 | 30.7 | 63 |

TABLE 6

10%, 30%, 50%, 70% and 90% inhibitory concentrations ($IC_{10}$, $IC_{30}$, $IC_{50}$, $IC_{70}$ and $IC_{90}$) of cisplatin, compound A, 5-FU and docetaxel in Detroit-562 cells.

| Anti-cancer agent | Detroit-562 cells (Inhibitory conc. In µM) | | | | |
|---|---|---|---|---|---|
| | $IC_{10}$ | $IC_{30}$ | $IC_{50}$ | $IC_{70}$ | $IC_{90}$ |
| Cisplatin | 0.3 | 3 | 14.6 | 43.2 | 74.5 |
| Compound A | 0.1 | 0.5 | 1.3 | 12.1 | 26.3 |
| 5-FU | 0.31 | 1.1 | 6.3 | 17.6 | 33.4 |
| Docetaxel | 0.009 | 0.3 | 0.85 | 8.7 | 21.8 |

TABLE 7

10%, 30%, 50%, 70% and 90% inhibitory concentrations ($IC_{10}$, $IC_{30}$, $IC_{50}$, $IC_{70}$ and $IC_{90}$) of cisplatin, compound A, 5-FU and docetaxel in FADU cells

| Anti-cancer agent | FADU cells (Inhibitory conc. In µM) | | | | |
|---|---|---|---|---|---|
| | $IC_{10}$ | $IC_{30}$ | $IC_{50}$ | $IC_{70}$ | $IC_{90}$ |
| Cisplatin | 0.25 | 3 | 8.3 | 30 | 74 |
| Compound A | 0.08 | 0.2 | 1.3 | 8.3 | 28.3 |
| 5-FU | 0.31 | 2.3 | 11.6 | 22.4 | 38.3 |
| Docetaxel | 0.003 | 0.06 | 0.16 | 0.71 | 35.6 |

Example 4

Combination Studies of Compound A and Sorafenib in SCC-25, Detroit-562 and FADU Cells.

A) SCC-25 Cells

Figure 6A:
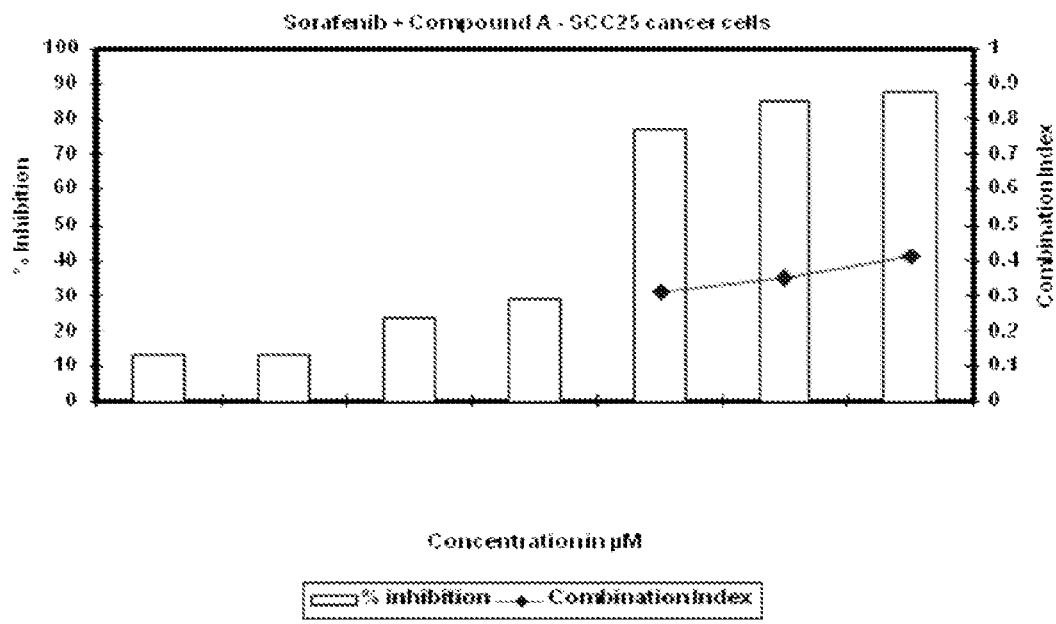
FIG. 6a is graphical representation of the percentage cytotoxicity results of single and combination dosing of compound A and sorafenib in SCC-25 cells.

Sorafenib in the following dose of final concentration 0.18 µM and compound A in the following doses of final concentration 0.1 µM, 0.4 µM and 4.1 µM were analyzed in single dose and in all possible combinations of the dose range for the two anticancer agents mentioned above. The sequence of treatment is as follows; the SCC-25 cells were treated with sorafenib for 0 to 24 hrs. At the end of 24 hrs the cells were washed two times with plain MEM (minimum essential media) medium. Fresh MEM with 10% serum (200 µL/well) was added, followed by treatment with compound A from 24 hrs to 96 hrs. The results are presented in the following Table 8 and graphically presented in FIG. 6a.

| Sr. No. | Anticancer agent (SCC-25 cells) (Inhibitory conc. in µM) | % Cytotoxicity | Combination index |
|---|---|---|---|
| 1 | Sorafenib $IC_{30}$ | 13 | — |
| 2 | Compound A $IC_{30}$ | 13 | — |
| 3 | Compound A $IC_{50}$ | 24 | — |
| 4 | Compound A $IC_{70}$ | 29 | — |
| 5 | Sorafenib $IC_{30}$ + Compound A $IC_{30}$ | 77 | 0.31 |
| 6 | Sorafenib $IC_{30}$ + Compound A $IC_{50}$ | 85 | 0.35 |
| 7 | Sorafenib $IC_{30}$ + Compound A $IC_{70}$ | 88 | 0.41 |

B) Detroit-562 Cells.

Figure 7A:
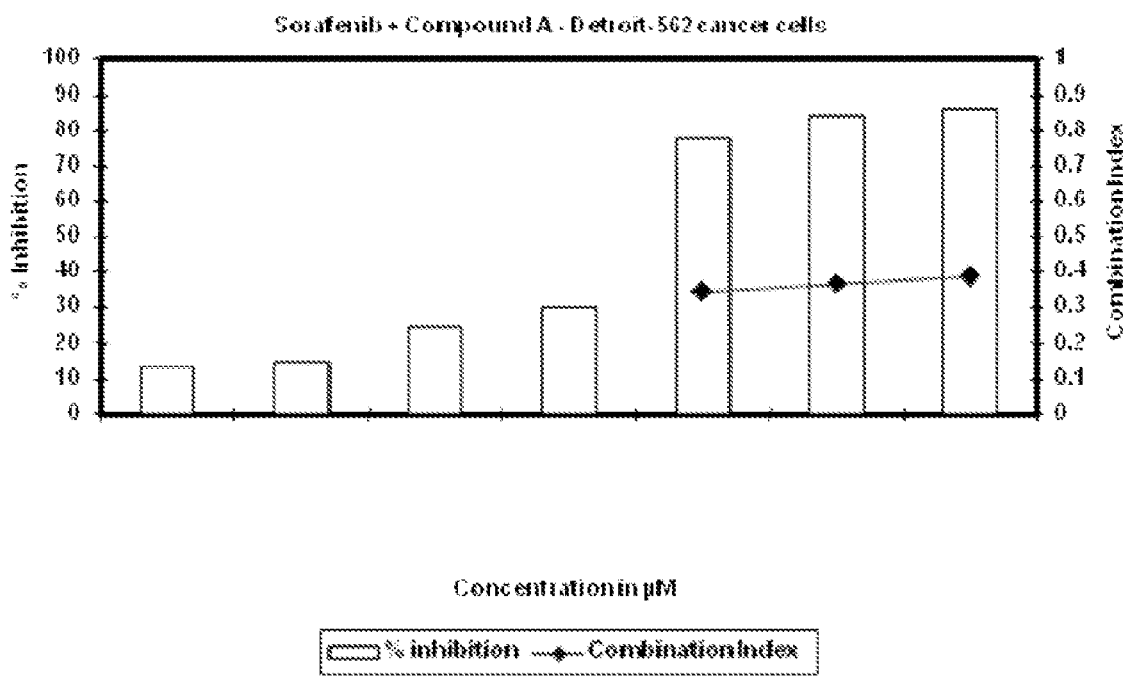
FIG. 7a is graphical representation of the percentage cytotoxicity results of single and combination dosing of compound A and sorafenib in Detroit-562 cells.

Sorafenib in the following dose of final concentration 1.8 µM and compound A in the following doses of final concentration 0.5 µM, 1.3 µM and 12.1 µM were analyzed in single dose and in all possible combinations of the dose range for the two anticancer agents mentioned above. The sequence of treatment is as follows; Detroit-562 cells were treated with sorafenib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 9 and graphically presented in FIG. 7a.

| Sr. No. | Anticancer agent (Detroit-562 cells) (Inhibitory conc. in µM) | % Cytotoxicity | Combination index |
|---|---|---|---|
| 1 | Sorafenib $IC_{30}$ | 14 | — |
| 2 | Compound A $IC_{30}$ | 15 | — |
| 3 | Compound A $IC_{50}$ | 25 | — |
| 4 | Compound A $IC_{70}$ | 30 | — |
| 5 | Sorafenib $IC_{30}$ + Compound A $IC_{30}$ | 78 | 0.35 |
| 6 | Sorafenib $IC_{30}$ + Compound A $IC_{50}$ | 84 | 0.37 |
| 7 | Sorafenib $IC_{30}$ + Compound A $IC_{70}$ | 86 | 0.39 |

C) FADU Cells

Figure 8A:
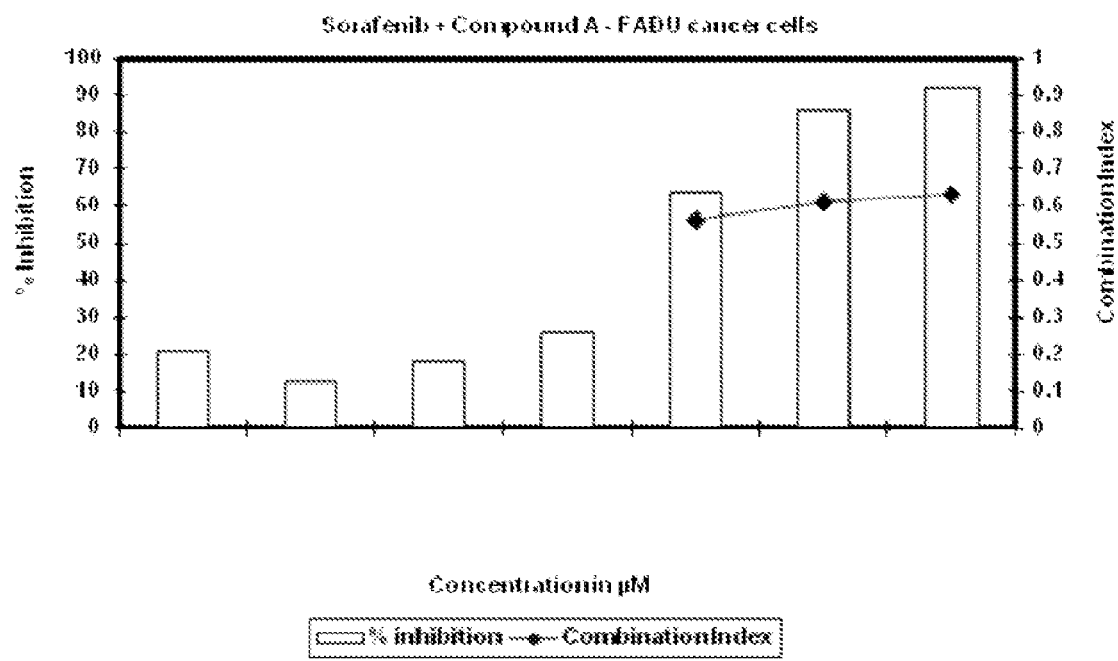
FIG. 8a is graphical representation of the percentage cytotoxicity results of single and combination dosing of compound A and sorafenib in FADU cells.

Sorafenib in the following dose of final concentration 3.9 µM and compound A in the following doses of final concentration 0.2 µM, 1.3 µM and 8.3 µM were analyzed in single dose and in all possible combinations of the dose range for the two anticancer agents mentioned above. The sequence of treatment is as follows; the FADU cells were treated with sorafenib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 10 and graphically presented in FIG. 8a.

| Sr. No. | Anticancer agent (FADU cells) (Inhibitory conc. in µM) | % Cytotoxicity | Combination index |
|---|---|---|---|
| 1 | Sorafenib $IC_{30}$ | 21 | — |
| 2 | Compound A $IC_{30}$ | 12 | — |
| 3 | Compound A $IC_{50}$ | 18 | — |
| 4 | Compound A $IC_{70}$ | 26 | — |
| 5 | Sorafenib $IC_{30}$ + Compound A $IC_{30}$ | 64 | 0.56 |
| 6 | Sorafenib $IC_{30}$ + Compound A $IC_{50}$ | 86 | 0.61 |
| 7 | Sorafenib $IC_{30}$ + Compound A $IC_{70}$ | 92 | 0.63 |

Example 5

Combination Studies of Compound B and Sorafenib in SCC-25, Detroit-562 and FADU Cells.

A) SCC-25 Cells

Figure 6B:
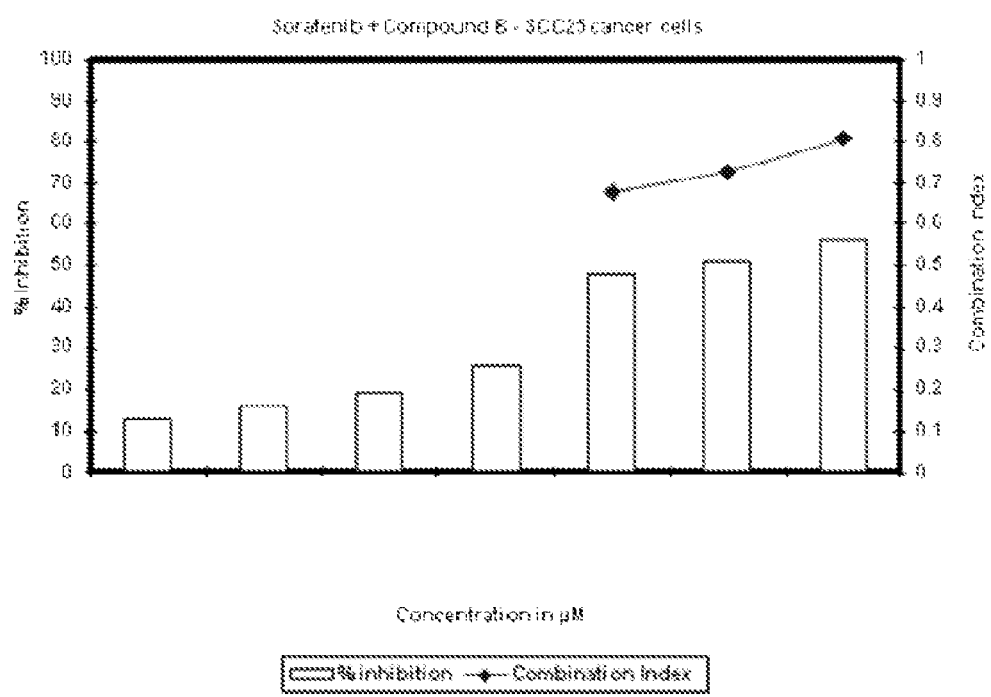
FIG. 6b is graphical representation of the percentage cytotoxicity results of single and combination dosing of compound B and sorafenib in SCC-25 cells.

Sorafenib in the following dose of final concentration 0.18 µM and compound B in the following doses of final concentration 0.2 µM, 1.1 µM and 4.8 µM were analyzed in single dose and in all possible combinations of the dose range for the two anticancer agents mentioned above. The sequence of treatment is as follows; the SCC-25 cells were treated with sorafenib for 0 to 24 hrs. At the end of 24 hrs the cells were washed two times with plain MEM medium. Fresh MEM with 10% serum (200 µL/well) was added, followed by treatment with compound B from 24 hrs to 96 hrs. The results are presented in the following Table 11 and graphically presented in FIG. 6b.

| Sr. No. | Anticancer agent (SCC-25 cells) (Inhibitory conc. in µM) | % Cytotoxicity | Combination index |
|---|---|---|---|
| 1 | Sorafenib $IC_{30}$ | 13 | — |
| 2 | Compound B $IC_{30}$ | 16 | — |
| 3 | Compound B $IC_{50}$ | 19 | — |
| 4 | Compound B $IC_{70}$ | 26 | — |
| 5 | Sorafenib $IC_{30}$ + Compound B $IC_{30}$ | 48 | 0.68 |
| 6 | Sorafenib $IC_{30}$ + Compound B $IC_{50}$ | 51 | 0.73 |
| 7 | Sorafenib $IC_{30}$ + Compound B $IC_{70}$ | 56 | 0.81 |

B) Detroit-562 Cells

Figure 7B:
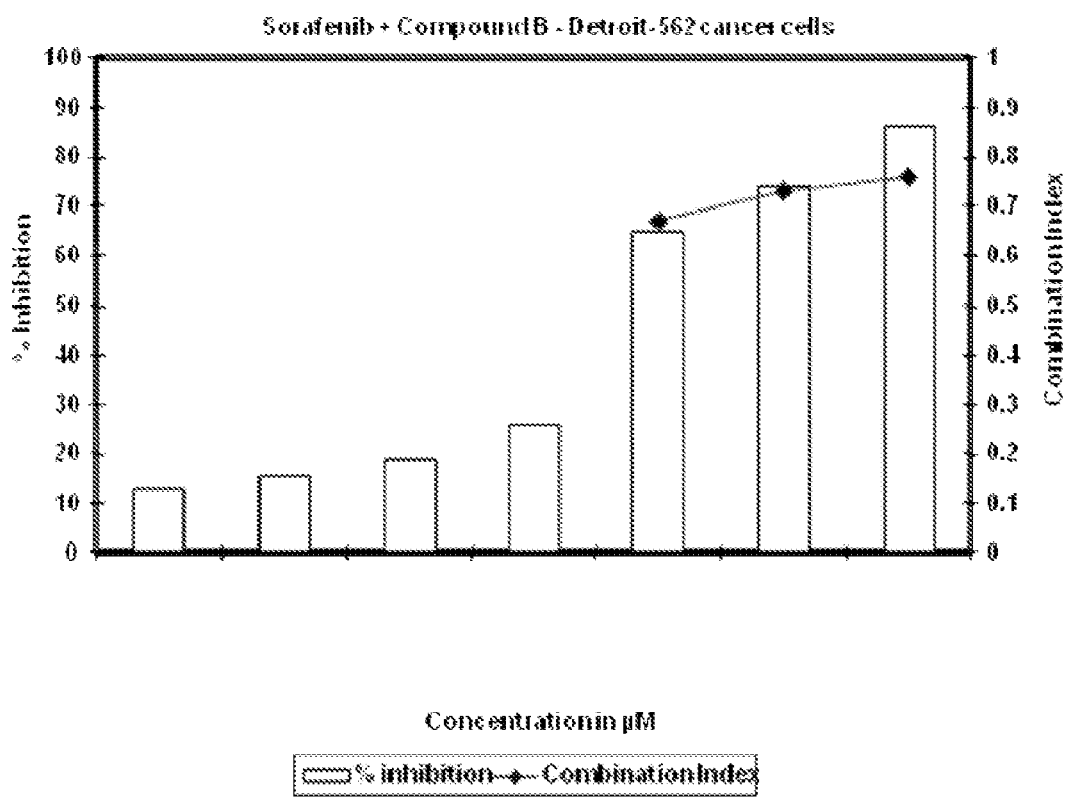
FIG. 7b is graphical representation of the percentage cytotoxicity results of single and combination dosing of compound B and sorafenib in Detroit-562 cells.

Sorafenib in the following dose of final concentration 1.8 µM and compound B in the following doses of final concentration 2.7 µM, 14.1 µM and 25.2 µM were analyzed in single dose and in all possible combinations of the dose range for the two anticancer agents mentioned above. The sequence of treatment is as follows; the Detroit-562 cells were treated with sorafenib for 0 to 24 hrs. At the end of 24 hrs the cells were washed two times with plain MEM medium. Fresh MEM with 10% serum (200 µL/well) was added, followed by treatment with compound B from 24 hrs to 96 hrs. The results are presented in the following Table 12 and graphically presented in FIG. 7b.

| Sr. No. | Anticancer agent (Detroit-562 cells) (Inhibitory conc. in µM) | % Cytotoxicity | Combination index |
|---|---|---|---|
| 1 | Sorafenib $IC_{30}$ | 13 | — |
| 2 | Compound B $IC_{30}$ | 15 | — |
| 3 | Compound B $IC_{50}$ | 19 | — |
| 4 | Compound B $IC_{70}$ | 26 | — |
| 5 | Sorafenib $IC_{30}$ + Compound B $IC_{30}$ | 65 | 0.67 |
| 6 | Sorafenib $IC_{30}$ + Compound B $IC_{50}$ | 74 | 0.73 |
| 7 | Sorafenib $IC_{30}$ + Compound B $IC_{70}$ | 86 | 0.76 |

C) FADU Cells

Figure 8B:
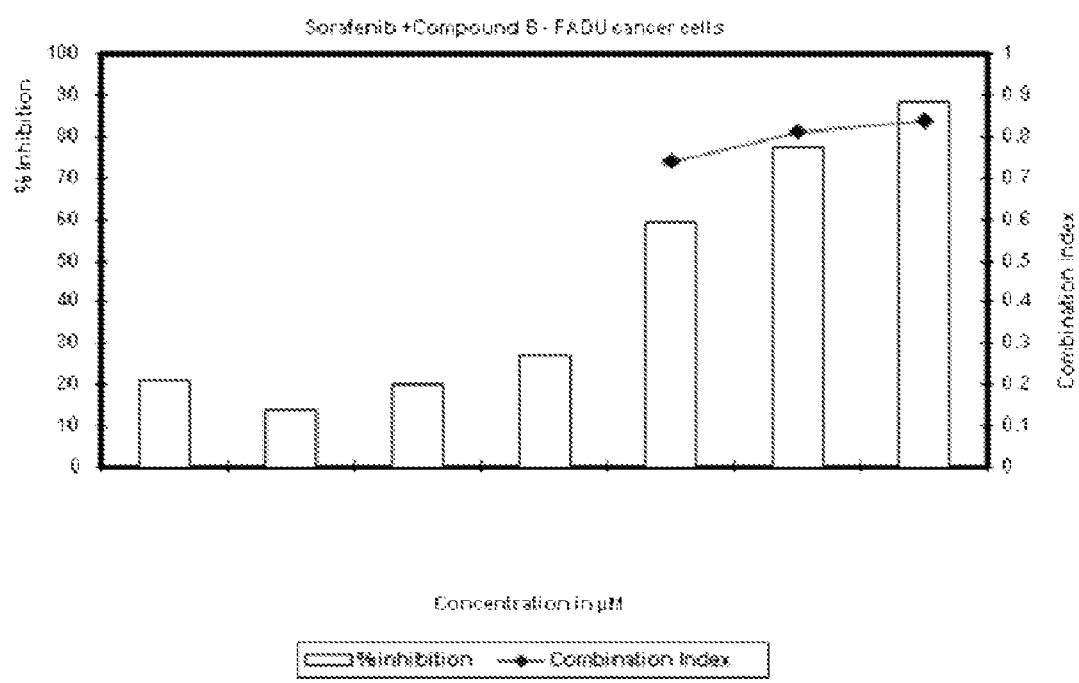
FIG. 8b is graphical representation of the percentage cytotoxicity results of single and combination dosing of compound B and sorafenib in FADU cells.

Sorafenib in the following dose of final concentration 3.9 µM and compound B in the following doses of final concentration 2.3 µM, 4.1 µM and 9.6 µM were analyzed in single dose and in all possible combinations of the dose range for the two drugs mentioned above. The sequence of treatment is as follows; the FADU cells were treated with sorafenib for 0 to 24 hrs. At the end of 24 hrs the cells were washed two times with plain MEM medium. Fresh MEM with 10% serum (200 µL/well) was added, followed by treatment with compound B from 24 hrs to 96 hrs. The results are presented in the following Table 13 and graphically presented in FIG. 8b.

| Sr. No. | Anticancer agent (FADU cells) (Inhibitory conc. in µM) | % Cytotoxicity | Combination index |
|---|---|---|---|
| 1 | Sorafenib $IC_{30}$ | 21 | — |
| 2 | Compound B $IC_{30}$ | 14 | — |
| 3 | Compound B $IC_{50}$ | 20 | — |
| 4 | Compound B $IC_{70}$ | 27 | — |
| 5 | Sorafenib $IC_{30}$ + Compound B $IC_{30}$ | 59 | 0.74 |
| 6 | Sorafenib $IC_{30}$ + Compound B $IC_{50}$ | 77 | 0.81 |
| 7 | Sorafenib $IC_{30}$ + Compound B $IC_{70}$ | 88 | 0.84 |

Example 6

Combination Studies of Compound A and Lapatinib in SCC-25, Detroit-562 and FADU Cells.

A) SCC-25 Cancer Cells

Figure 9A:
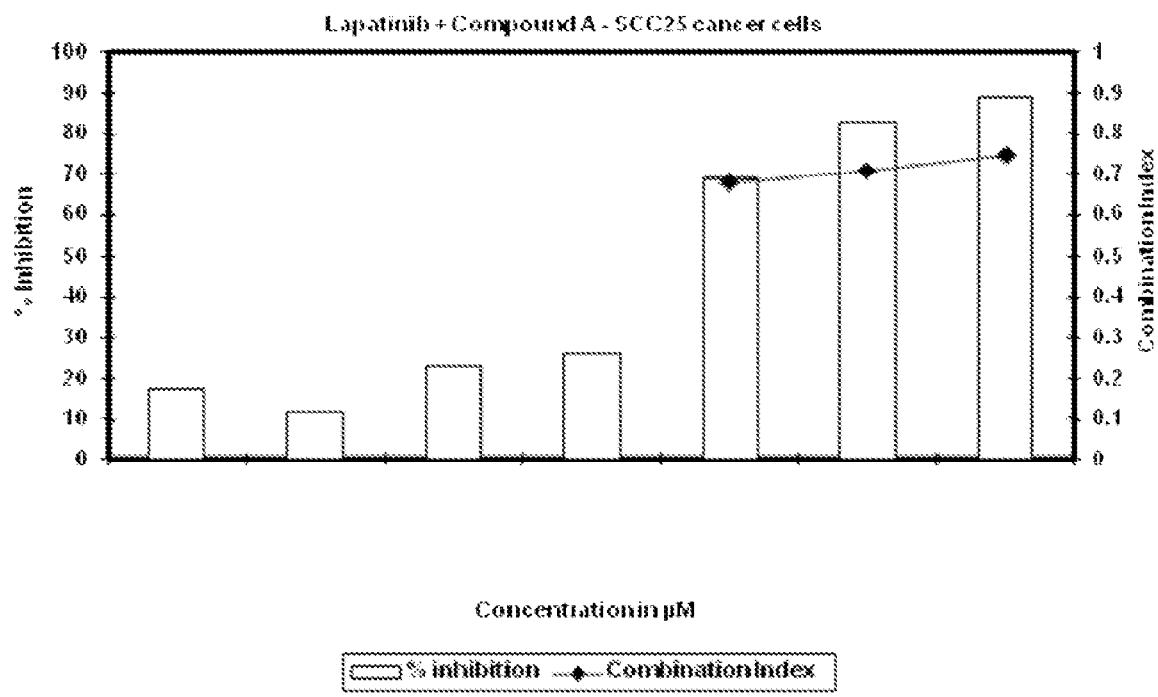
FIG. 9a is graphical representation of the percentage cytotoxicity results of single and combination dosing of compound A and lapatinib in SCC-25 cells.

Lapatinib in the following dose of final concentration 0.2 µM and compound A in the following doses of final concentration 0.2 µM, 0.5 µM and 3.3 µM were analyzed in single dose and in all possible combinations of the dose range for the two drugs mentioned above. The sequence of treatment is as follows; the SCC-25 cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 14 and graphically presented in FIG. 9a.

| Sr. No. | Anticancer agent (SCC-25 cells) (Inhibitory conc. in µM) | % Cytotoxicity | Combination index |
|---|---|---|---|
| 1 | Lapatinib $IC_{30}$ | 17 | — |
| 2 | Compound A $IC_{30}$ | 12 | — |
| 3 | Compound A $IC_{50}$ | 23 | — |
| 4 | Compound A $IC_{70}$ | 26 | — |
| 5 | Lapatinib $IC_{30}$ + Compound A $IC_{30}$ | 69 | 0.68 |
| 6 | Lapatinib $IC_{30}$ + Compound A $IC_{50}$ | 83 | 0.71 |
| 7 | Lapatinib $IC_{30}$ + Compound A $IC_{70}$ | 89 | 0.75 |

B) Detroit-562 Cancer Cells

Figure 10A:
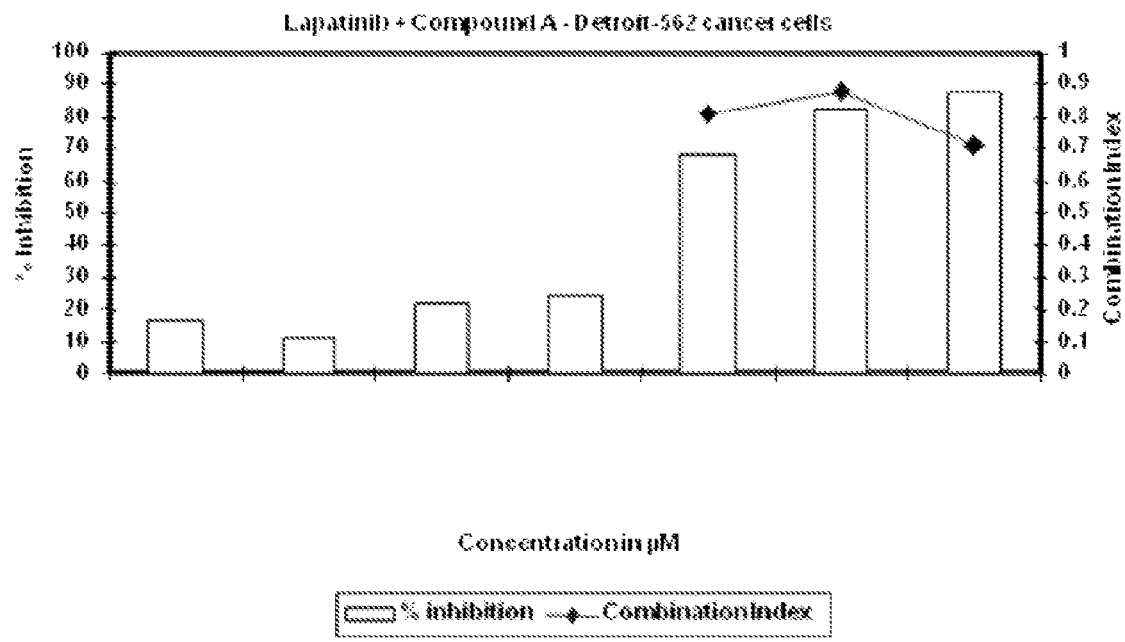
FIG. 10a is graphical representation of the percentage cytotoxicity results of single and combination dosing of compound A and lapatinib in Detroit-562 cells.

Lapatinib in the following dose of final concentration 1 µM and compound A in the following doses of final concentration 0.5 µM, 1.3 µM and 12.1 µM were analyzed in single dose and in all possible combinations of the dose range for the two anticancer agents mentioned above. The sequence of treatment is as follows; the Detroit-562 cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 15 and graphically presented in FIG. 10a.

| Sr. No. | Anticancer agent (Detroit-562 cells) (Inhibitory conc. in µM) | % Cytotoxicity | Combination index |
|---|---|---|---|
| 1 | Lapatinib $IC_{30}$ | 16 | — |
| 2 | Compound A $IC_{30}$ | 11 | — |
| 3 | Compound A $IC_{50}$ | 22 | — |
| 4 | Compound A $IC_{70}$ | 25 | — |
| 5 | Lapatinib $IC_{30}$ + Compound A $IC_{30}$ | 68 | 0.81 |
| 6 | Lapatinib $IC_{30}$ + Compound A $IC_{50}$ | 82 | 0.88 |
| 7 | Lapatinib $IC_{30}$ + Compound A $IC_{70}$ | 88 | 0.71 |

C) FADU Cancer Cells

Figure 11A:
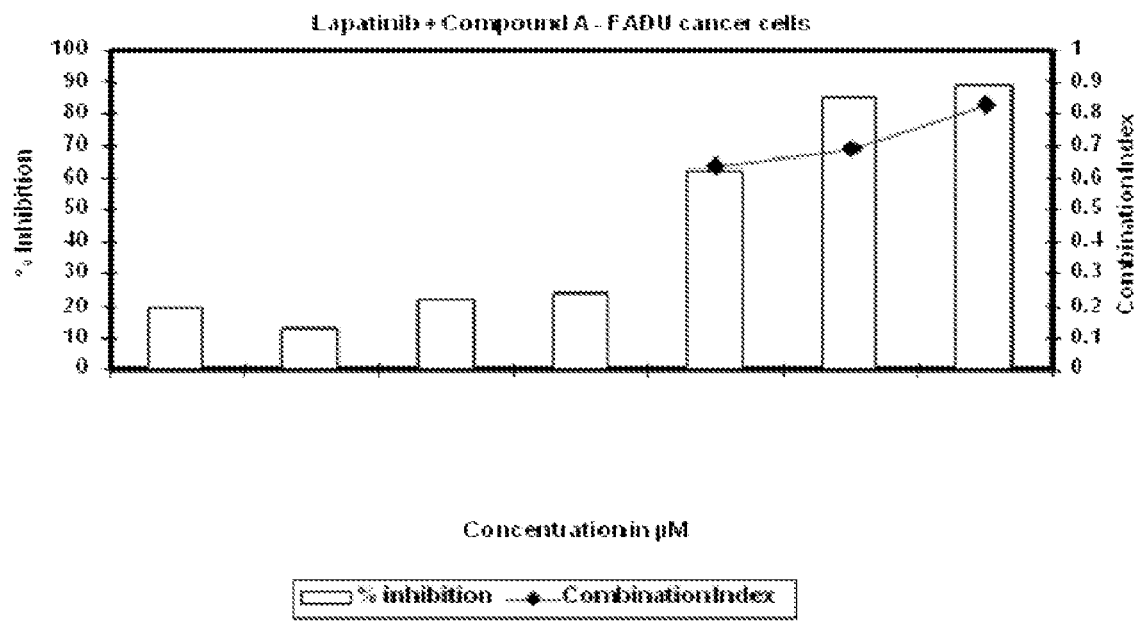
FIG. 11a is graphical representation of the percentage cytotoxicity results of single and combination dosing of compound A and lapatinib in FADU cells.

Lapatinib in the following dose of final concentration 0.8 µM and compound A in the following doses of final concentration 0.2 µM, 1.3 µM and 8.3 µM were analyzed in single dose and in all possible combinations of the dose range for the two drugs mentioned above. The sequence of treatment is as follows; the FADU cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 16 and graphically presented in FIG. 11a.

| Sr. No. | Anticancer agent (FADU cells) (Inhibitory conc. in µM) | % Cytotoxicity | Combination index |
|---|---|---|---|
| 1 | Lapatinib $IC_{30}$ | 19 | — |
| 2 | Compound A $IC_{30}$ | 13 | — |
| 3 | Compound A $IC_{50}$ | 22 | — |
| 4 | Compound A $IC_{70}$ | 24 | — |
| 5 | Lapatinib $IC_{30}$ + Compound A $IC_{30}$ | 62 | 0.64 |
| 6 | Lapatinib $IC_{30}$ + Compound A $IC_{50}$ | 85 | 0.69 |
| 7 | Lapatinib $IC_{30}$ + Compound A $IC_{70}$ | 89 | 0.83 |

Example 7

Figure 9B:
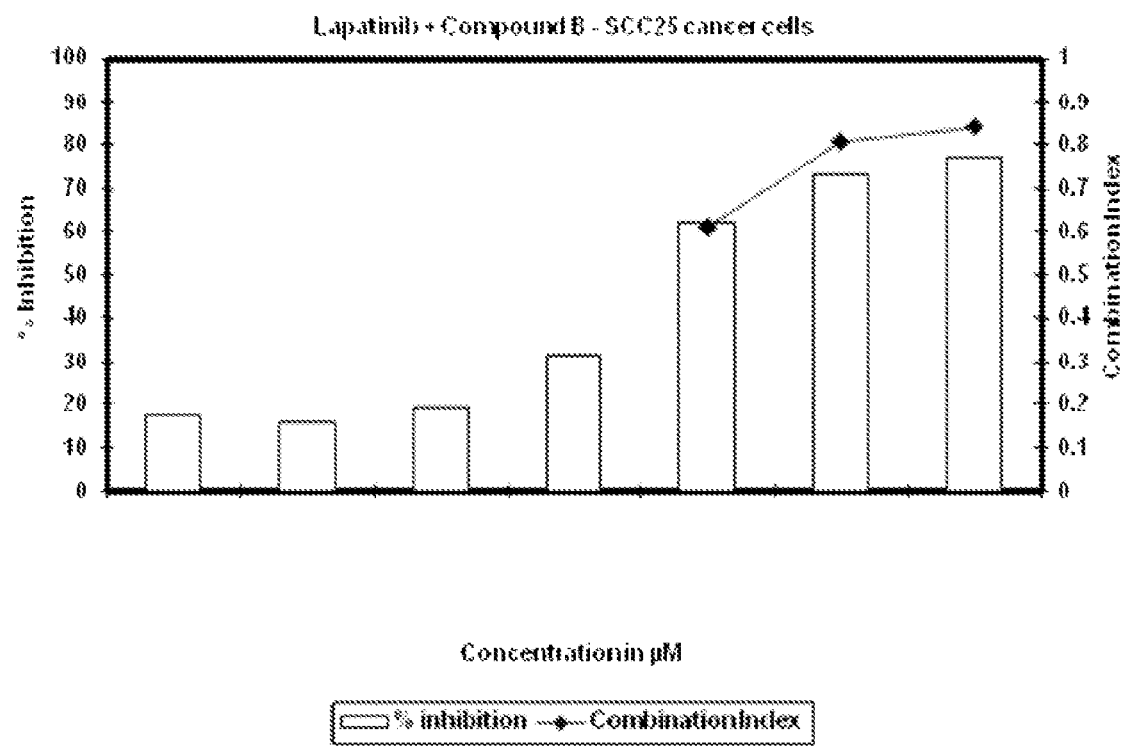
FIG. 9b is graphical representation of the percentage cytotoxicity results of single and combination dosing of compound B and lapatinib in SCC-25 cells.

Combination Studies of Compound B and Lapatinib in SCC-25, Detroit-562 and FADU Cells A) SCC-25 Cancer Cells Lapatinib in the following dose of final concentration 0.2 µM and compound B in the following doses of final concentration 0.2 µM, 1.1 µM and 4.8 µM were analyzed in single dose and in all possible combinations of the dose range for the two drugs mentioned above. The sequence of treatment is as follows; the SCC-25 cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 17 and graphically presented in FIG. 9b.

| Sr. No. | Anticancer agent (SCC-25 cells) (Inhibitory conc. in µM) | % Cytotoxicity | Combination index |
|---|---|---|---|
| 1 | Lapatinib $IC_{30}$ | 17 | — |
| 2 | Compound B $IC_{30}$ | 16 | — |
| 3 | Compound B $IC_{50}$ | 19 | — |
| 4 | Compound B $IC_{70}$ | 31 | — |
| 5 | Lapatinib $IC_{30}$ + Compound B $IC_{30}$ | 62 | 0.61 |
| 6 | Lapatinib $IC_{30}$ + Compound B $IC_{50}$ | 73 | 0.81 |
| 7 | Lapatinib $IC_{30}$ + Compound B $IC_{70}$ | 77 | 0.84 |

B) Detroit-562 Cancer Cells

Figure 10B:
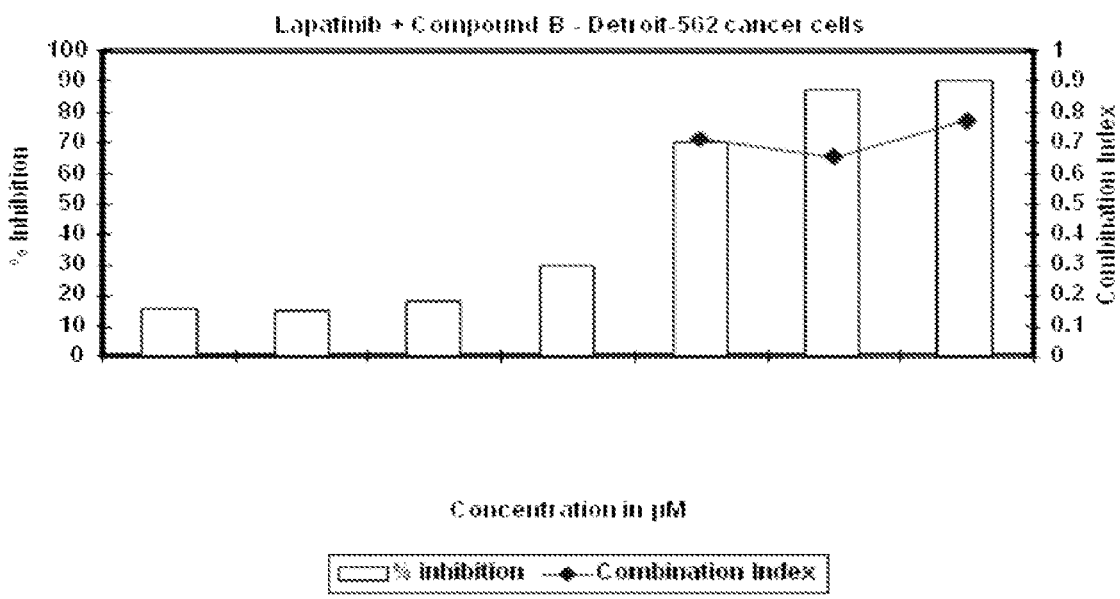
FIG. 10b is graphical representation of the percentage cytotoxicity results of single and combination dosing of compound B and lapatinib in Detroit-562 cells.

Lapatinib in the following dose of final concentration 1.0 µM and compound B in the following doses of final concentration 2.7 µM, 14.1 µM and 25.2 µM were analyzed in single dose and in all possible combinations of the dose range for the two drugs mentioned above. The sequence of treatment is as follows; the Detroit-562 cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 18 and graphically presented in FIG. 10b.

| Sr. No. | Anticancer agent (Detroit-562 cells) (Inhibitory conc. in µM) | % Cytotoxicity | Combination index |
|---|---|---|---|
| 1 | Lapatinib $IC_{30}$ | 16 | — |
| 2 | Compound B $IC_{30}$ | 15 | — |
| 3 | Compound B $IC_{50}$ | 18 | — |
| 4 | Compound B $IC_{70}$ | 30 | — |
| 5 | Lapatinib $IC_{30}$ + Compound B $IC_{30}$ | 70 | 0.71 |
| 6 | Lapatinib $IC_{30}$ + Compound B $IC_{50}$ | 87 | 0.65 |
| 7 | Lapatinib $IC_{30}$ + Compound B $IC_{70}$ | 90 | 0.77 |

C) FADU Cancer Cells

Figure 11B:
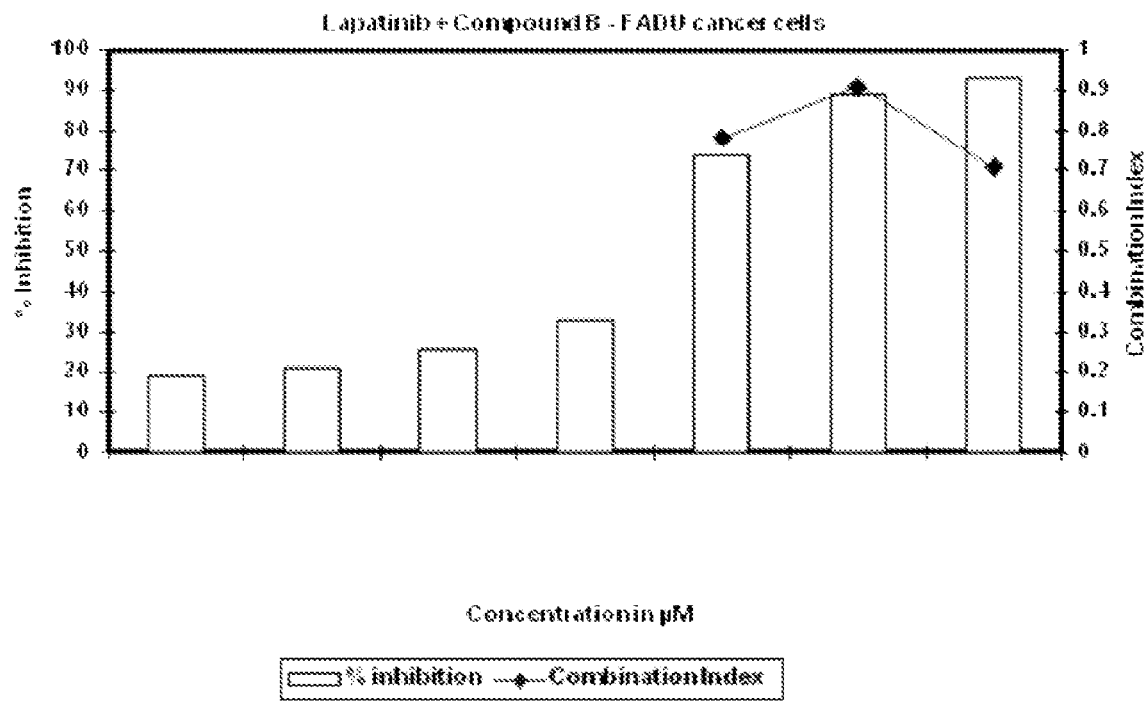
FIG. 11b is graphical representation of the percentage cytotoxicity results of single and combination dosing of compound B and lapatinib in FADU cells.

Lapatinib in the following dose of final concentration 0.8 µM and compound B in the following doses of final concentration 2.3 µM, 4.1 µM and 9.6 µM were analyzed in single dose and in all possible combinations of the dose range for the two anticancer agents mentioned above. The sequence of treatment is as follows; the FADU cells were treated with lapatinib for 0 to 24 hrs. At the end of 24 hrs the cells were washed two times with plain MEM medium. Fresh MEM with 10% serum (200 µL/well) was added, followed by treatment with compound A from 24 hrs to 96 hrs. The results are presented in the following Table 19 and graphically presented in FIG. 11b.

| Sr. No. | Anticancer agent (FADU cells) (Inhibitory conc. in µM) | % Cytotoxicity | Combination index |
|---|---|---|---|
| 1 | Lapatinib $IC_{30}$ | 19 | — |
| 2 | Compound B $IC_{30}$ | 21 | — |
| 3 | Compound B $IC_{50}$ | 26 | — |
| 4 | Compound B $IC_{70}$ | 33 | — |
| 5 | Lapatinib $IC_{30}$ + Compound B $IC_{30}$ | 74 | 0.78 |
| 6 | Lapatinib $IC_{30}$ + Compound B $IC_{50}$ | 89 | 0.91 |
| 7 | Lapatinib $IC_{30}$ + Compound B $IC_{70}$ | 93 | 0.71 |

Example 8

Figure 12A:
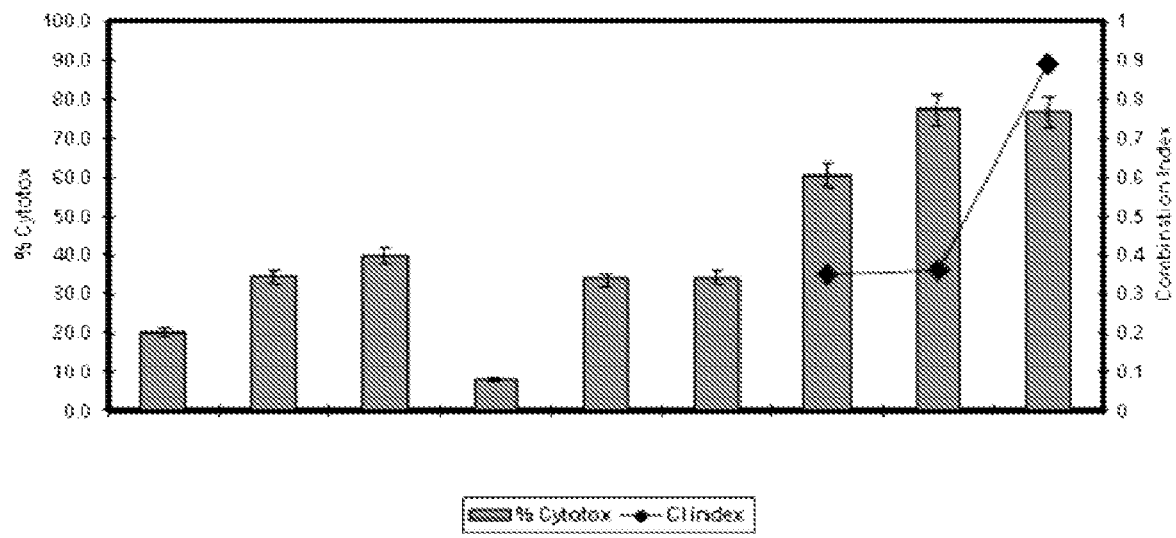
FIG. 12a is graphical representation of the percentage cytotoxicity results of single and combination dosing of compound A and erlotinib in Detroit-562 cells.

Combination Studies of Compound A and Erlotinib at $IC_{30}$ Concentration in Detroit-562 Cells The combination of erlotinib and compound A was found to be synergistic at the $IC_{30}$ of both the anticancer agents. Erlotinib at $IC_{30}$ showed cytotoxicity of 20.3% and Compound A at $IC_{30}$, showed cytotoxicity of 8.30%. However, when used as a combination of erlotinib $IC_{30}$ for 24 hrs, followed by compound A $IC_{30}$ for 48 hrs showed an increase in cytotoxicity to the extent of 60% was noted, which is 32% more cytotoxicity than the additive effect suggesting a synergistic effect between the two anticancer agents in Detroit-562 cells with a combination index of 0.35. The results are presented in the following Table 20 and graphically presented in FIG. 12a.

| Sr. No. | Anticancer agent (Detroit 562 cells) (Inhibitory conc. in µM) | % Cytotoxicity | Combination index |
|---|---|---|---|
| 1 | Erlotinib IC30 | 20.3 | — |
| 2 | Erlotinib IC50 | 34.4 | — |
| 3 | Erlotinib IC70 | 40.0 | — |
| 4 | Compound A IC30 | 8.30 | — |
| 5 | Compound A IC50 | 33.80 | — |
| 6 | Compound A IC70 | 34.32 | — |
| 7 | Erlotinib IC30 + Compound A IC30 | 60.64 | 0.35 |
| 8 | Erlotinib IC30 + Compound AIC50 | 77.17 | 0.36 |
| 9 | Erlotinib IC30 + Compound A IC70 | 76.89 | 0.89 |

Example 9

Combination Studies of Compound A and Erlotinib in FADU Cells

Figure 12B:
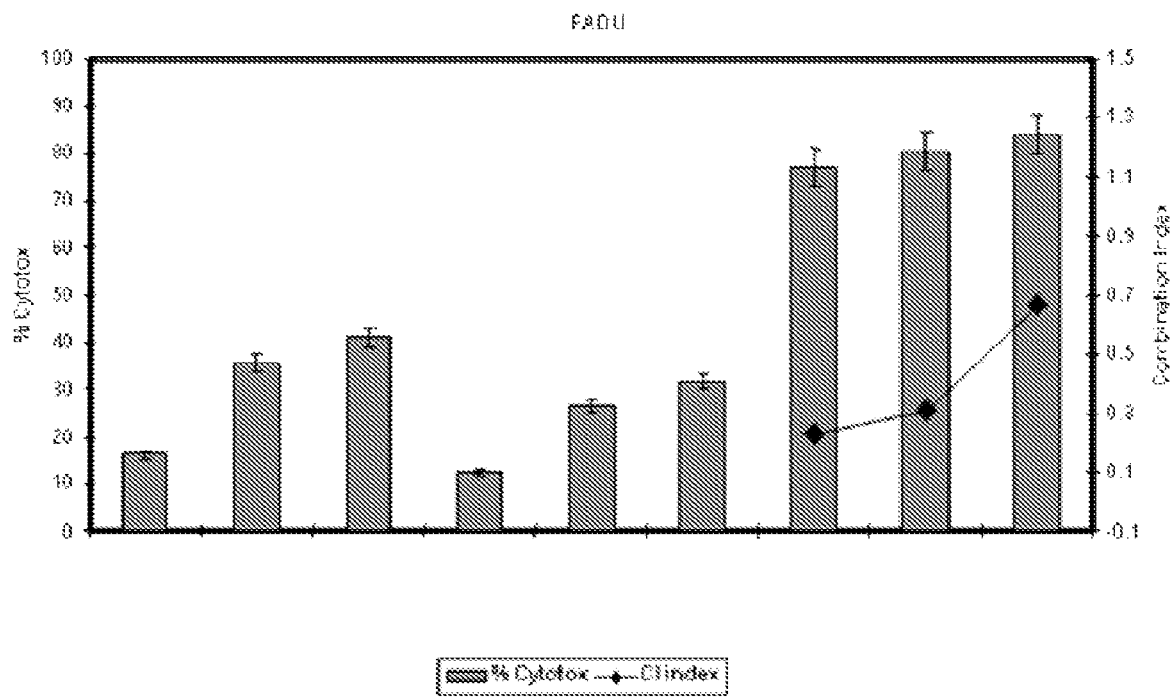
FIG. 12b is graphical representation of the percentage cytotoxicity results of single and combination dosing of compound A and erlotinib in FADU cells.

The combination of erlotinib and Compound A was found to be synergistic at the $IC_{30}$ of both the anticancer agents. erlotinib at $IC_{30}$ showed cytotoxicity of 16% and Compound A at $IC_{30}$, showed cytotoxicity of 12.3%. However, when used as a combination of erlotinib at concentration $IC_{30}$ for 24 hrs, followed by compound A at $IC_{30}$ concentration for 48 hrs showed an increase in cytotoxicity to the extent of 77% was noted, which is 49% more cytotoxicity than the additive effect suggesting a synergistic effect between the two drugs in FADU cells with a combination index of 0.23. The results are presented in the following Table 21 and graphically presented in FIG. 12b.

| Sr. No. | Anticancer agent (FADU cells) (Inhibitory conc. in μM) | % Cytotoxicity | Combination index |
|---|---|---|---|
| 1 | Erlotinib IC30 | 16.24 | — |
| 2 | Erlotinib IC50 | 35.64 | — |
| 3 | Erlotinib IC70 | 41.1 | — |
| 4 | Compound A IC30 | 12.3 | — |
| 5 | Compound A IC50 | 26.54 | — |
| 6 | Compound A IC70 | 31.78 | — |
| 7 | Erlotinib IC30 + Compound A IC30 | 77.191 | 0.23 |
| 8 | Erlotinib IC30 + Compound A IC50 | 80.286 | 0.31 |
| 9 | Erlotinib IC30 + Compound A IC70 | 84.134 | 0.67 |

In Vitro Studies Involving Use of Triple Combination Consisting of compound A, Cisplatin and 5-FU

Example 10

Combination Studies of Compound A, Cisplatin and 5-FU at the $IC_{30}$ in Detroit-562 Cells.

Figure 13A:
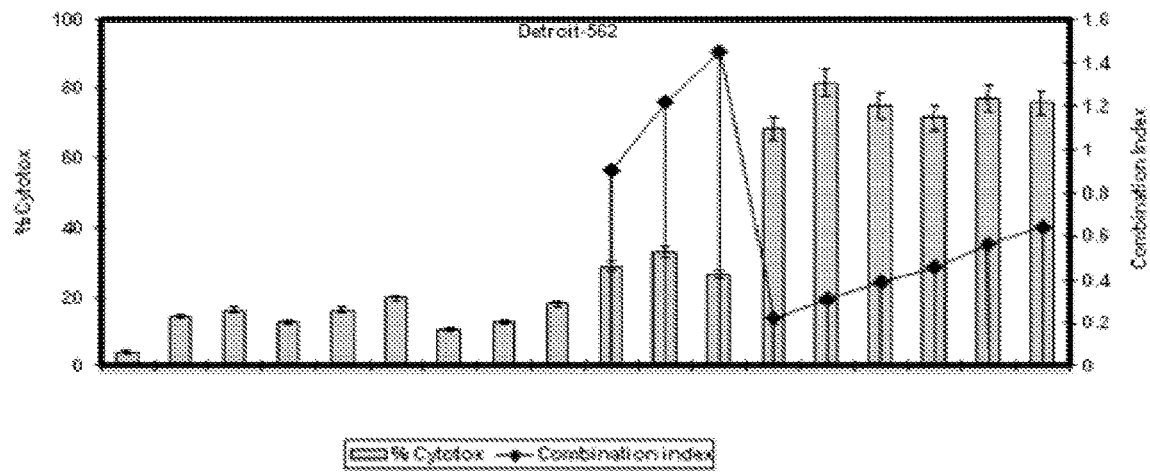
FIG. 13a is graphical representation of the percentage cytotoxicity results of single and combination dosing of compound A, cisplatin and 5-FU in Detroit-562 cells.

The combination of compound A and (cisplatin and 5-FU) was found to be synergistic at the $IC_{30}$ of each anticancer agents. Compound A at $IC_{30}$ showed cytotoxicity of 10.4% and (cisplatin and 5-FU) at $IC_{30}$, showed cytotoxicity of 28.60%. However, when used as a combination of (cisplatin and 5-FU) $IC_{30}$ for 24 hrs, followed by compound A $IC_{30}$ for 48 hrs an increase in cytotoxicity to the extent of 71% was noted, which was 33% more cytotoxicity than the additive effect suggesting a synergistic effect between the three anticancer agents in Detroit-562 cells with a combination index of 0.39. While the double combination Cisplatin and 5-FU showed a combination index of 0.9. The results are presented in the following Table 22 and graphically presented in FIG. 13a.

| Sr. No. | Anticancer agent (Detroit 562 cells) (Inhibitory conc. in μM) | % Cytotoxicity | Combination index |
|---|---|---|---|
| 1 | Cisplatin IC30 | 4.07 | — |
| 2 | Cisplatin IC50 | 14.3 | — |
| 3 | Cisplatin IC70 | 16.2 | — |
| 4 | 5-FU IC90 | 12.59 | — |
| 5 | 5-FU IC50 | 16.21 | — |
| 6 | 5-FU IC70 | 19.54 | — |
| 7 | Compound A IC30 | 10.42 | — |
| 8 | Compound A IC50 | 12.59 | — |
| 9 | Compound A IC70 | 18.02 | — |
| 10 | Cisplatin IC30 + 5-FU IC30 | 28.67 | 0.9 |
| 11 | Cisplatin IC30 + 5-FU IC50 | 32.86 | 1.21 |
| 12 | Cisplatin IC30 + 5-FU IC70 | 26.38 | 1.45 |
| 13 | Cisplatin IC30 + 5-FU IC30 + Compound A IC30 | 68.38 | 0.22 |
| 14 | Cisplatin IC30 + 5-FU IC50 + Compound A IC30 | 81.68 | 0.31 |
| 15 | Cisplatin IC30 + 5-FU IC70 + Compound A IC30 | 75.22 | 0.39 |
| 16 | Cisplatin IC30 + 5-FU IC30 + Compound A IC50 | 77.30 | 0.56 |
| 17 | Cisplatin IC30) + 5-FU IC30 + Compound A IC70 | 75.75 | 0.64 |

Example 11

Combination Studies of Compound A, Cisplatin and 5-FU at the $IC_{30}$ in FADU Cells.

Figure 13B:
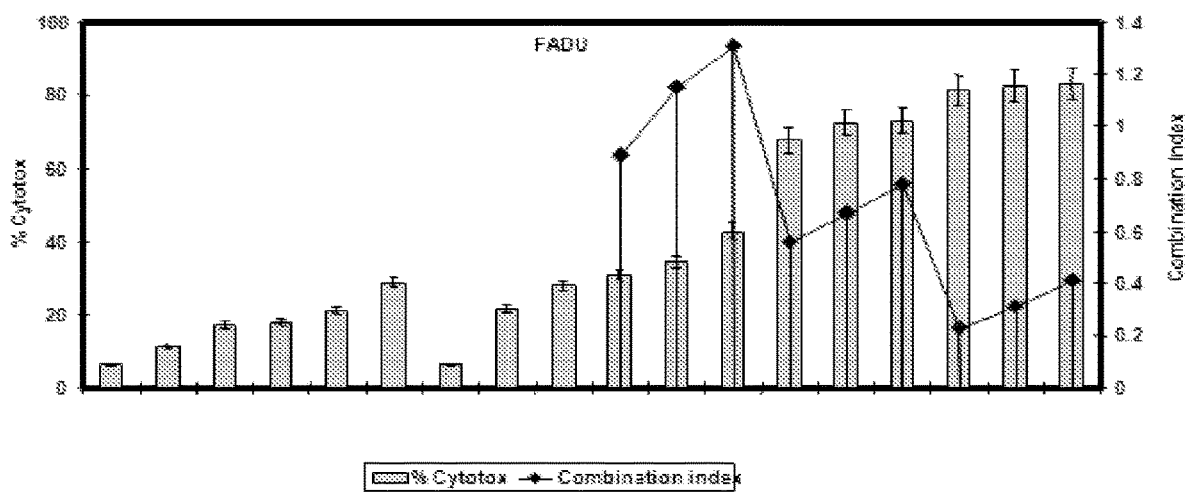
FIG. 13b is graphical representation of the percentage cytotoxicity results of single and combination dosing of compound A, cisplatin and 5-fluorouracil in FADU cells.

The combination of compound A and (cisplatin and 5-FU) was found to be synergistic at the $IC_{30}$ of each anticancer agent. Compound A at $IC_{30}$ showed cytotoxicity of 6.1% and (cisplatin and 5-FU) at $IC_{30}$, showed cytotoxicity of 30.1%. However, when used as a combination of (cisplatin and 5-FU) at $IC_{30}$ concentration for 24 hrs, followed by compound A $IC_{30}$ for 48 hrs, an increase in cytotoxicity to the extent of 81% was noted, which was 44% more cytotoxicity than the additive effect suggesting a synergistic effect between the three drugs in FADU cells with a combination index of 0.23. While the double combination cisplatin and 5-FU showed a combination index of 0.89. The results are presented in the following Table 23 and graphically presented in FIG. 13b.

| Sr. No. | Anticancer agent (FADU cells) (Inhibitory conc. in μM) | % Cytotoxicity | Combination index |
|---|---|---|---|
| 1 | Cisplatin IC30 | 6.2 | — |
| 2 | Cisplatin IC50 | 11.1 | — |
| 3 | Cisplatin IC70 | 17.1 | — |
| 4 | 5-FU IC30 | 17.81 | — |
| 5 | 5-FU IC50 | 21.1 | — |
| 6 | 5-FU IC70 | 28.6 | — |
| 7 | Compound A IC30 | 6.1 | — |
| 8 | Compound A IC50 | 21.4 | — |
| 9 | Compound A IC70 | 27.8 | — |
| 10 | Cisplatin IC30 + 5-FU IC30 | 30.8 | 0.89 |
| 11 | Cisplatin IC30 + 5-FU IC50 | 34.53 | 1.15 |
| 12 | Cisplatin IC30 + 5-FU IC70 | 42.82 | 1.31 |
| 13 | Cisplatin IC30 + 5-FU IC30 + Compound A IC30 | 67.73 | 0.56 |
| 14 | Cisplatin IC30 + 5-FU IC50 + Compound A IC30 | 72.43 | 0.67 |
| 15 | Cisplatin IC30 + 5-FU IC70 + Compound A IC30 | 72.94 | 0.78 |
| 18 | Cisplatin IC30 + 5-FU IC30 + Compound A IC50 | 82.40 | 0.31 |
| 19 | Cisplatin IC30 + 5-FU IC30 + Compound A IC70 | 83.13 | 0.41 |

Example 12

Combination Studies of Compound A, Cisplatin and 5-FU with Docetaxel at the IC30 Concentration in Detroit-562 Cells.

The combination of compound A and (cisplatin and 5-FU) with Docetaxel was found to be synergistic at the $IC_{30}$ of each anticancer agent. Compound A and Docetaxel at $IC_{30}$ showed cytotoxicity of 16.8% and 18.30 respectively (cisplatin and 5-FU) at $IC_{30}$, showed cytotoxicity of 31.3%.

Figure 14A:
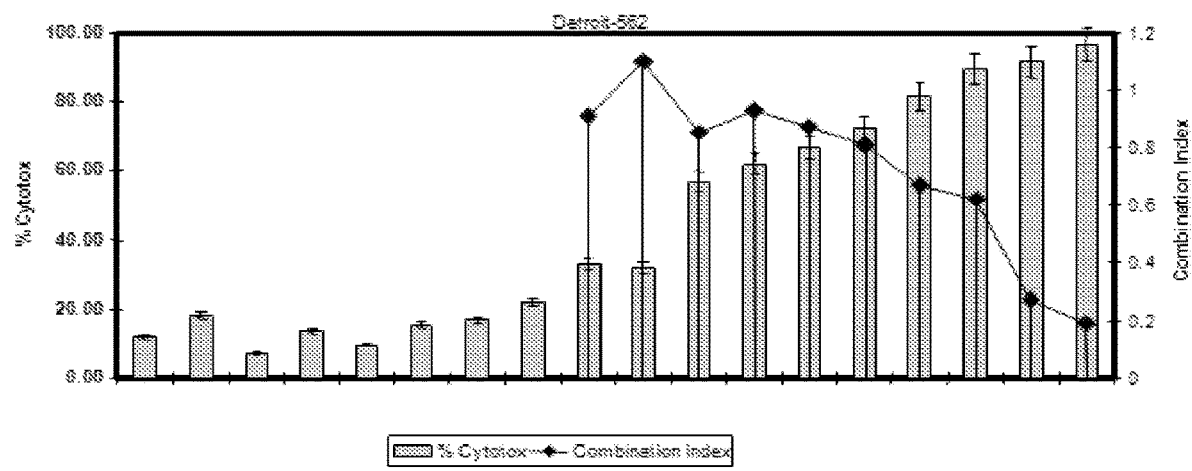
FIG. 14a is graphical representation of the percentage cytotoxicity results of single and combination dosing of compound A, docetaxel, cisplatin and 5-FU in Detroit-562 cells.

However, when used as a combination of Docetaxel at $IC_{30}$ concentration for 12 hrs followed by (cisplatin and 5-FU) at $IC_{30}$ concentration for 12 hrs, followed by compound A at $IC_{30}$ concentration for 48 hrs an increase in cytotoxicity to the extent of 96.38% was noted, with a combination index of 0.29. The results are presented in the following Table 24 and graphically presented in FIG. 14a.

| Sr. No. | Anticancer agent (Detroit 562 cells) (Inhibitory conc. in μM) | % Cytotoxicity | Combination index (C.I. values) |
|---|---|---|---|
| 1 | Docetaxel $IC_{10}$ | 11.75 | — |
| 2 | Docetaxel $IC_{30}$ | 18.30 | — |
| 3 | Cisplatin $IC_{10}$ | 6.92 | — |
| 4 | Cisplatin $IC_{30}$ | 13.39 | — |
| 5 | 5-FU $IC_{10}$ | 9.49 | — |
| 6 | 5-FU $IC_{30}$ | 15.39 | — |
| 7 | Compound A $IC_{30}$ | 16.81 | — |
| 8 | Compound A $IC_{50}$ | 21.98 | — |
| 9 | Cisplatin $IC_{10}$ + 5FU $IC_{10}$ | 33.09 | 0.91 |
| 10 | Cisplatin $IC_{30}$ + 5FU $IC_{30}$ | 31.92 | 1.1 |
| 11 | Docetaxel $IC_{10}$ + (Cisplatin $IC_{10}$ + 5FU $IC_{10}$) | 56.85 | 0.85 |
| 12 | Docetaxel $IC_{10}$ + (Cisplatin $IC_{30}$ + 5FU $IC_{30}$) | 61.77 | 0.93 |
| 13 | Docetaxel $IC_{30}$ + (Cisplatin $IC_{10}$ + 5FU $IC_{10}$) | 66.59 | 0.87 |
| 14 | Docetaxel $IC_{30}$ + (Cisplatin $IC_{30}$ + 5FU $IC_{30}$) | 71.81 | 0.81 |
| 15 | Docetaxel $IC_{10}$ + (Cisplatin $IC_{10}$ + 5FU $IC_{10}$) + Compound A $IC_{30}$ | 81.42 | 0.67 |
| 18 | Docetaxel $IC_{10}$ + (Cisplatin $IC_{30}$ + 5FU $IC_{30}$) + Compound A $IC_{30}$ | 89.46 | 0.62 |
| 19 | Docetaxel $IC_{30}$ + (Cisplatin $IC_{10}$ + 5FU $IC_{10}$) + Compound A $IC_{30}$ | 91.47 | 0.37 |
| 20 | Docetaxel $IC_{30}$ + (Cisplatin $IC_{30}$ + 5FU $IC_{30}$) + Compound A $IC_{30}$ | 96.38 | 0.29 |

Example 13

Combination Studies of Compound A, Cisplatin and 5-FU with Docetaxel at the $IC_{30}$ Concentration in FADU Cells.

Figure 14B:
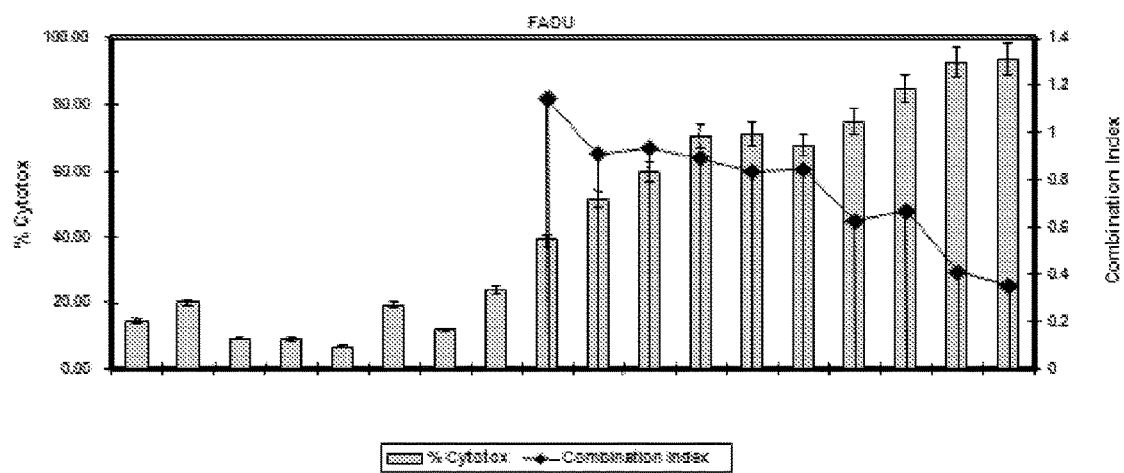
FIG. 14b is graphical representation of the percentage cytotoxicity results of single and combination dosing of compound A, docetaxel, cisplatin and 5-FU in FADU cells.

The combination of compound A and (cisplatin and 5-FU) with docetaxel was found to be synergistic at the $IC_{30}$ of each anticancer agent. Compound A and docetaxel at $IC_{30}$ concentration showed cytotoxicity of 11.77% and 20.02 respectively. (cisplatin and 5-FU) at $IC_{30}$ concentration, showed cytotoxicity of 51.39%. However, when used as a combination of docetaxel at $IC_{30}$ concentration for 12 hrs followed by (cisplatin and 5-FU) at $IC_{30}$ concentration for 12 hrs, followed by compound A at $IC_{30}$ concentration for 48 hrs an increase in cytotoxicity to the extent of 98.24% was noted, with a combination index of 0.12. The results are presented in the following Table 25 and graphically presented in FIG. 14b.

| Anticancer agent (FADU cells) (Inhibitory conc. in μM) | % Cytotoxicity | Combination index (C.I. values) |
|---|---|---|
| Docetaxel $IC_{10}$ | 14.69 | — |
| Docetaxel $IC_{30}$ | 20.02 | — |
| Cisplatin $IC_{10}$ | 9.16 | — |
| Cisplatin $IC_{30}$ | 9.08 | — |
| 5-FU $IC_{10}$ | 6.81 | — |
| 5-FU $IC_{30}$ | 19.29 | — |
| Compound A $IC_{30}$ | 11.77 | — |
| Compound A $IC_{50}$ | 23.86 | — |
| Cisplatin $IC_{10}$ + 5FU $IC_{10}$ | 39.03 | 1.15 |
| Cisplatin $IC_{30}$ + 5FU $IC_{30}$ | 51.39 | 0.91 |
| Docetaxel $IC_{10}$ + (Cisplatin $IC_{10}$ + 5FU $IC_{10}$) | 59.95 | 0.94 |
| Docetaxel $IC_{10}$ + (Cisplatin $IC_{30}$ + 5FU $IC_{30}$) | 70.28 | 0.89 |
| Docetaxel $IC_{30}$ + (Cisplatin $IC_{10}$ + 5FU $IC_{10}$) | 71.16 | 0.84 |
| Docetaxel $IC_{30}$ + (Cisplatin $IC_{30}$ + 5FU $IC_{30}$) | 67.80 | 0.85 |
| Docetaxel $IC_{10}$ + (Cisplatin $IC_{10}$ + 5FU $IC_{10}$) + Compound A $IC_{30}$ | 74.93 | 0.63 |
| Docetaxel $IC_{10}$ + (Cisplatin $IC_{30}$ + 5FU $IC_{30}$) + Compound A $IC_{30}$ | 84.83 | 0.67 |
| Docetaxel $IC_{30}$ + (Cisplatin $IC_{10}$ + 5FU $IC_{10}$) + Compound A $IC30$ | 92.67 | 0.31 |
| Docetaxel $IC_{30}$ + (Cisplatin $IC_{30}$ + 5FU $IC_{30}$) + Compound A $IC_{30}$ | 98.24 | 0.12 |

Example 14

Analysis of Cleaved Caspase-3 Expression Levels

This study was conducted to evaluate the mechanisms by which the combination consisting of sorafenib or lapatinib in combination with compound A or compound B blocks proliferation and whether it can induce apoptosis in head and neck cancer cells. The cells were seeded in 96-well plates at a density of $7.5 \times 10^3$ cells/well. 24 h post seeding, the minimum essential medium was replaced with a fresh minimum essential medium with 10% serum. The anticancer agents (sorafenib or lapatinib in combination with compound A or compound B) were treated with specific concentration as mentioned below in SCC-25, Detroit-562 and FADU cells and incubated for 48 hrs. At the end of 48 hrs, to determine the protein expression, the cells were in 96 well plate spin down at 800 g for 5 minutes. Culture supernatant was removed and 200 μL of caspase-3 assay buffer was added and plates were again spin down at 800 g for 5 minutes. Supernatant were removed and cells were lysed with 100 μL caspase-3 lysis buffer and incubated for 30 min in orbital shaker at 300 rpm at room temperature. Further plates were spin down at 800 g for 10 minutes and 90 μL of the supernatant was transferred into new black well plate. To 90 μL of lysis solution 100 μL of caspase-3 substrate was added and incubated for 30 minutes at 37'C. At the end of incubation plates were read in Tecan Safire multimode reader with an excitation wavelength of 485 nm and emission wavelength of 535 nm.

Figure 15A:
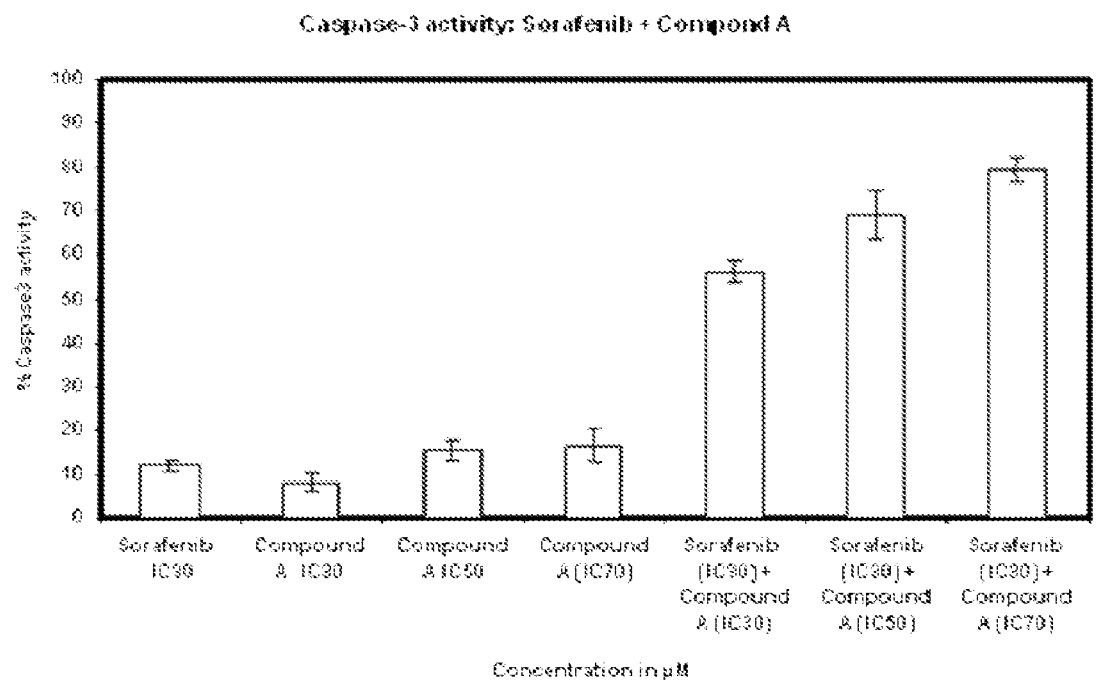
FIG. 15a is graphical representation of activation of Caspase 3 in SCC-25 cells with single and combination dosing of sorafenib and compound A.
Figure 15B:
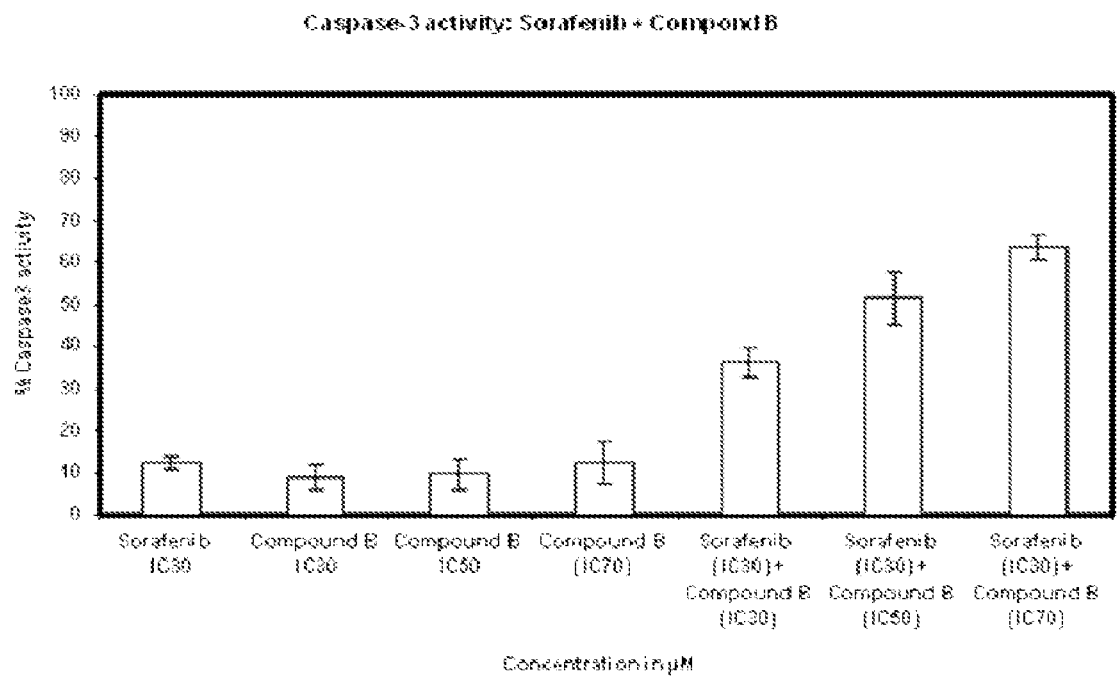
FIG. 15b is graphical representation of activation of Caspase 3 in SCC-25 cells with single and combination dosing of sorafenib and compound B.

A) Treatment Pattern of Sorafenib and Compound A or Compound B in SCC-25 Cells for Assessing Caspase-3 Activity The treatment with sorafenib for 24 hrs followed by either compound A or compound B for 48 hrs showed notable elevation of caspase3 expression than when used alone. It was also observed that both compound A or compound B were more potent in inducing caspase-3 activity in combination as graphically represented in FIG. 15a and FIG. 15b.

Figure 16A:
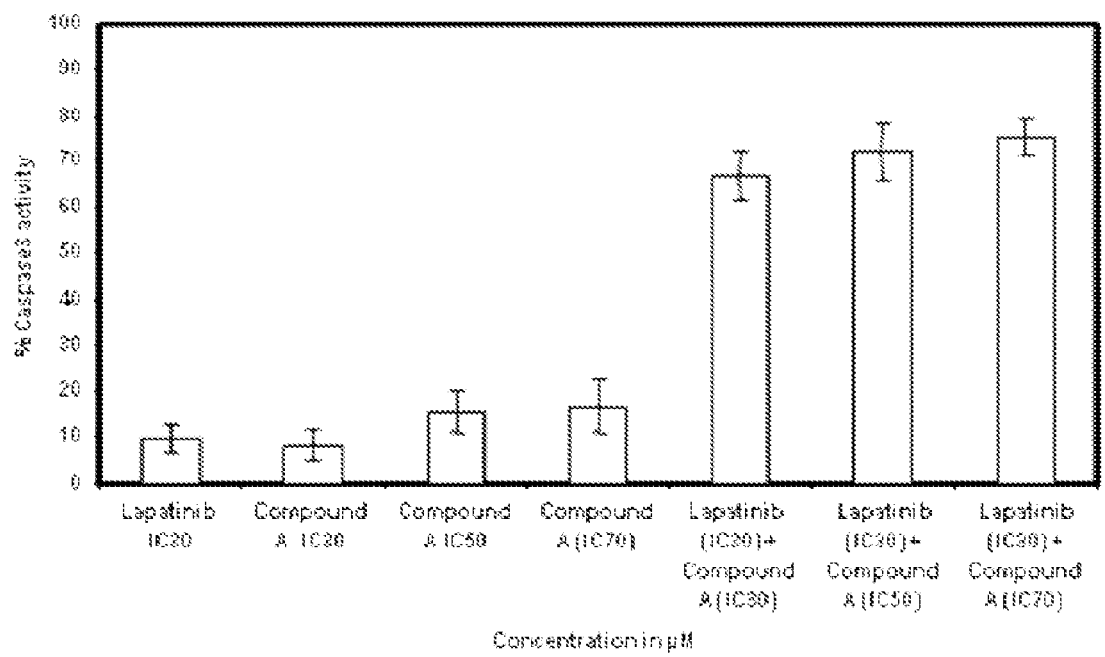
FIG. 16a is graphical representation of activation of Caspase 3 in SCC-25 cells with single and combination dosing of lapatinib and compound A.
Figure 16B:
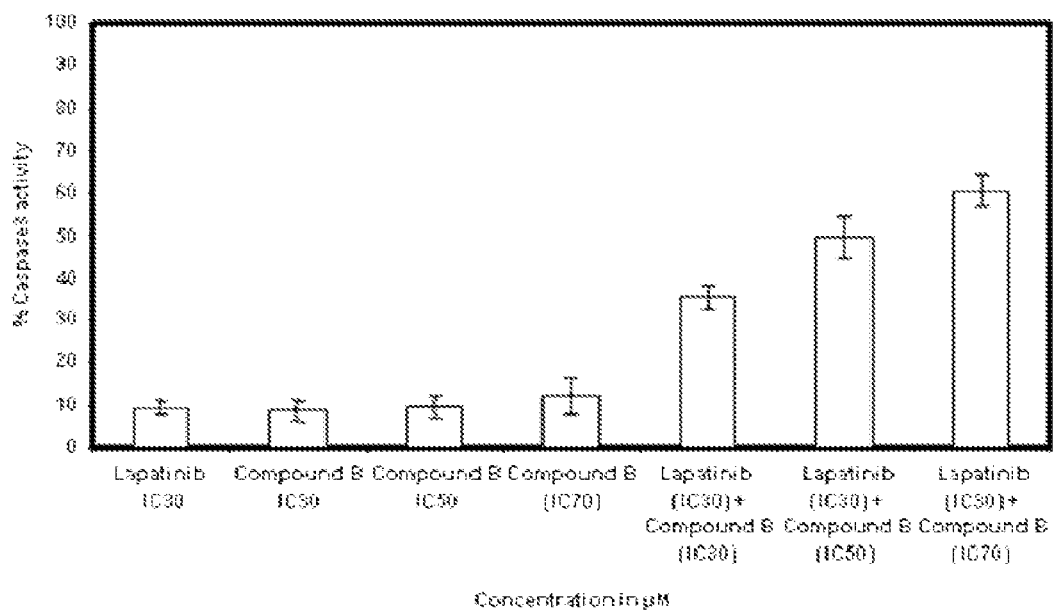
FIG. 16b is graphical representation of activation of Caspase 3 in SCC-25 cells with single and combination dosing of lapatinib and compound B.

B) Treatment Pattern of Lapatinib and Compound A or Compound B in SCC-25 Cells for Assessing Caspase-3 Activity The treatment with lapatinib for 24 hrs followed by either compound A or compound B for 48 hrs showed notable elevation of caspase3 expression than when used alone. It was also observed that both compound A or compound B were more potent in inducing caspase-3 activity in combination as graphically represented in FIG. 16a and FIG. 16b.

Example 15

In Vivo Efficacy Studies in Human Head and Neck Cancer FaDu (Hypopharyngeal Squamous Cell Carcinoma) Xenografts In-vivo studies were carried out according to the method described in Clinical cancer search, 2003, 9, 6052-6061; the disclosure of which is incorporated herein by reference for the teaching of the assay.

Objective

The objective of this study was to evaluate the antitumor activity of Compound A in combination with cetuximab or in combination with both, cisplatin and cetuximab in human head and neck cancer xenograft model of FaDu.

The in-vivo studies were carried out using Xenograft models in Severe combined immune deficiency (SCID) mice strain—CbySmn.CB17-Prkdcscid/J, by the method described below. The statistically significant number of mice per group (n=6) was chosen in order to be able to statistically evaluate the study data.

Method

FaDu cells were grown in MEM (minimum essential media) medium containing non-essential amino acids and 10% fetal calf serum in 5% CO2 incubator at 37° C. Cells were pelleted by centrifugation at 1000 rpm for 10 minutes. Cells were resuspended in pre-chilled mixture of saline to get a count of 6×106 cells per mL; 0.2 ml of this cell suspension was kept on ice and injected by subcutaneous (s.c.) route in SCID mice. Mice were observed every alternate day for palpable tumor mass. Once the tumor size reached a size of 3-5 mm in diameter, animals were randomized into respective groups of treatment and untreated controls. The treatment groups comprised of 5 groups viz. 1) Compound A alone (Group 1); 2) cetuximab alone (Group 2); 3) cisplatin alone (Group 3); 4) Compound A+cetuximab (Group 4); and 5) Compound A+cisplatin+cetuximab (Group 5). The control group received no treatment. In single drug treatment i.e. in respect of Groups 1, 2 and 3, the Compound A (35 mpk) was administered by i.p route once daily for 5 days a week starting from day 1 of the week for 3 weeks with total of 15 doses; Cisplatin (1 mpk) was administered i.p. once a week on day 1 of the week with total of 3 doses. Cetuximab (2.5 mpk) was administered twice a week on days 1 and 4 of the week for 3 weeks with total of 6 doses. In the treatment with combination of drugs namely compound A and cetuximab, the sequence that was followed included administration of Compound A for 2 h followed by cetuximab:

In the treatment with combination of drugs namely compound A, cisplatin and cetuximab, the sequence that was followed included administration of cisplatin for 2 h followed by the Compound A for 2 h, followed by cetuximab. Measurement of tumor was done every 2-3 days apart. Growth inhibition percentage (GI %) was calculated at the end of experiment.

Terminal Procedures:

At the end of the experiment, animals were euthanized using high dose of pentobarbital sodium (100 mg/kg i.p./i.v.) or exposure to carbon dioxide gas.

Results

Figure 17A:
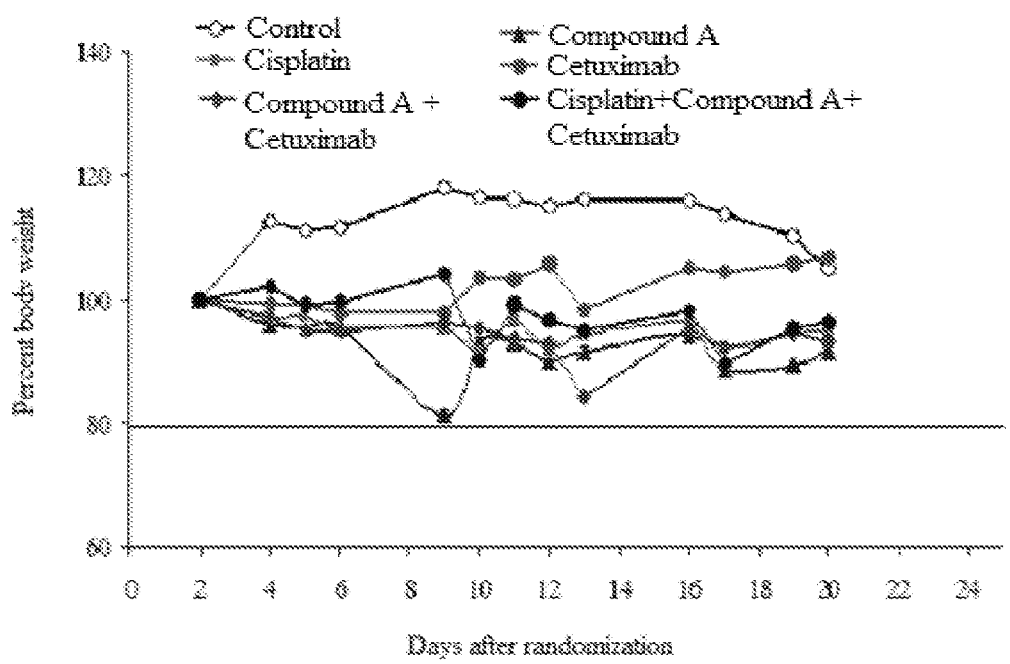
FIG. 17a is graphical representation of body weight profile in FaDu xenografts treated with single and combination dosing of compound A, cisplatin and cetuximab.
Figure 17B:
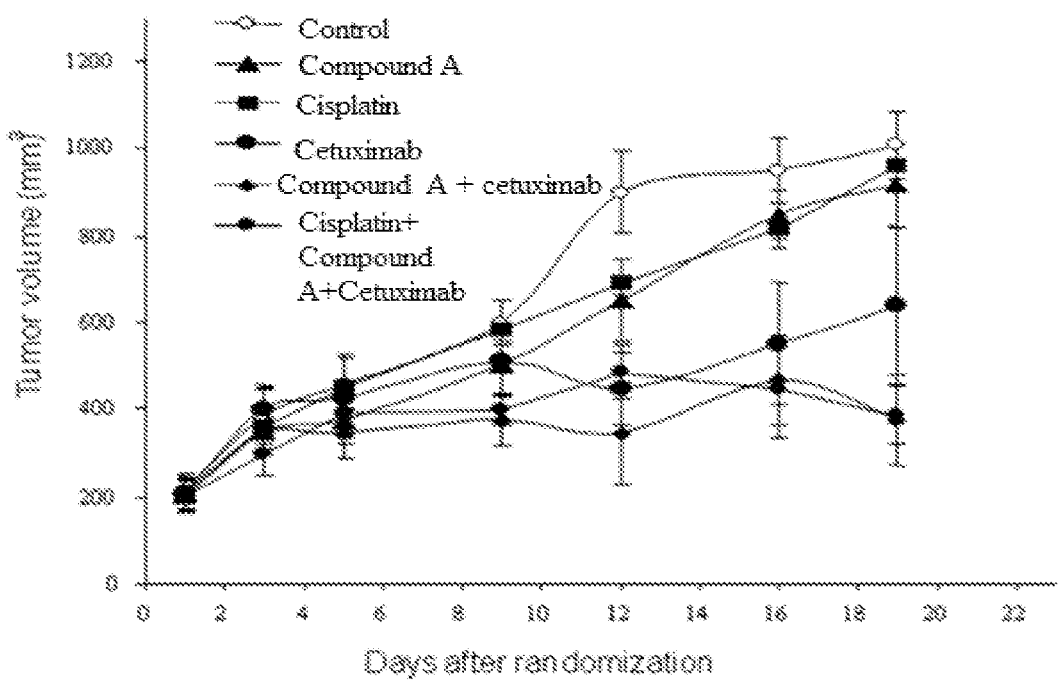
FIG. 17b is graphical representation of tumor growth inhibition in FaDu xenografts treated with single and combination dosing of compound A, cisplatin and cetuximab.

The results are as presented in Table 26 and graphically presented in FIG. 17a. The FIG. 17a depicts the average group body weight over the period of drug (the therapeutic agents) administration plotted. FIG. 17b depicts the average % tumor weight of Head and Neck carcinoma (Fadu) xenograft over a period of 18 days.

TABLE 26

Percent tumor growth inhibition at the end of treatment i.e. after 18 days.

| Groups | Tumor Growth inhibition (%) |
|---|---|
| Group 1 (Compound A) | 11 |
| Group 2 (cisplatin) | 4 |
| Group 3 (cetuximab) | 45 |
| Group 4 (combination of Compound A and cetuximab) | 79 |
| Group 5 (combination of cisplatin, Compound A and cetuximab) | 77 |

The tumor growth inhibition was highly significant with p<0.001 in the treatment groups namely Group(s) 4 and 5 involving use of combination of antineoplastic agents with tumor growth (TG) inhibition of 79% and. 77% respectively. There was no significant body weight loss in all the treatment groups.

Conclusion

The combination of Compound A and cetuximab and the combination of Compound A, cetuximab and cisplatin showed similar antitumor activity in the human head and neck cancer xenograft model of FaDu and were significantly higher than either of the drugs alone.

Having thus described in detail various embodiments of the present invention, it is to be understood that the invention defined by the above paragraphs is not to be limited to particular details set forth in the above description as many apparent variations thereof are possible without departing from the spirit or scope of the present invention.

We claim:

1. A method of treating tongue cancer or pharyngeal cancer in a subject in need thereof, the method comprising administering to the subject a therapeutically effective amount of a CDK inhibitor of Formula I, or a pharmaceutically acceptable salt or solvate thereof, and a therapeutically effective amount of one or more first antineoplastic agents selected from sorafenib and lapatinib, wherein in Formula I Ar is 2-chloro-4-trifluoromethylphenyl:

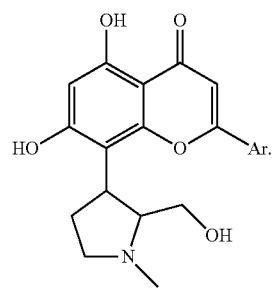

Formula I

2. The method of claim 1, wherein the pharmaceutically acceptable salt is (+)-trans-2-(2-chloro-4-trifluoromethylphenyl)-5,7-dihydroxy-8-(2-hydroxymethyl-1-methyl-pyrrolidin-3-yl)-chromen-4-one hydrochloride.

3. The method of claim 1, wherein the antineoplastic agent is sorafenib.

4. The method of claim 1, wherein the antineoplastic agent is lapatinib.

5. The method of claim 1, wherein the cancer is tongue cancer.

6. The method of claim 1, wherein the cancer is pharyngeal cancer.

7. The method of claim 1, further comprising administration of radiation.

8. The method of claim 1, further comprising administering to the subject a second antineoplastic agent selected from the group consisting of sorafenib, lapatinib, erlotinib, cisplatin, 5-fluorouracil, docetaxel, and cetuximab.

* * * * *